US011207308B2

(12) United States Patent
Waters et al.

(10) Patent No.: US 11,207,308 B2
(45) Date of Patent: Dec. 28, 2021

(54) PHARMACEUTICAL COMPOSITIONS FOR COMBINATION THERAPY

(71) Applicant: PRILENIA NEUROTHERAPEUTICS LTD., Herzliya (IL)

(72) Inventors: Ross Nicholas Waters, Göteborg (CH); Eva Susanna Holm Waters, Göteborg (CH)

(73) Assignee: PRILENIA NEUROTHERAPEUTICS LTD., Herzliya (IL)

( * ) Notice: Subject to any disclaimer, the term of this patent is extended or adjusted under 35 U.S.C. 154(b) by 0 days.

(21) Appl. No.: 16/203,182

(22) Filed: Nov. 28, 2018

(65) Prior Publication Data

US 2020/0000785 A1  Jan. 2, 2020

Related U.S. Application Data

(63) Continuation of application No. 16/054,054, filed on Aug. 3, 2018, now abandoned, which is a continuation of application No. 15/612,779, filed on Jun. 2, 2017, now abandoned, which is a continuation of application No. 13/856,254, filed on Apr. 3, 2013, now abandoned.

(60) Provisional application No. 61/783,730, filed on Mar. 14, 2013, provisional application No. 61/625,192, filed on Apr. 17, 2012, provisional application No. 61/620,203, filed on Apr. 4, 2012.

(51) Int. Cl.
*A61K 31/445* (2006.01)
*A61K 31/4375* (2006.01)
*A61K 31/451* (2006.01)
*A61K 31/4745* (2006.01)

(52) U.S. Cl.
CPC ........ *A61K 31/445* (2013.01); *A61K 31/4375* (2013.01); *A61K 31/451* (2013.01); *A61K 31/4745* (2013.01)

(58) Field of Classification Search
CPC .............. A61K 31/445; A61K 31/4375; A61K 31/451; A61K 31/4745
USPC ....................................................... 514/243
See application file for complete search history.

(56) References Cited

U.S. PATENT DOCUMENTS

| | | |
|---|---|---|
| 3,326,916 A | 6/1967 | Creighton et al. |
| 3,458,521 A | 7/1969 | Jack et al. |
| 3,539,573 A | 11/1970 | Schmutz et al. |
| 4,048,314 A | 9/1977 | Kubela et al. |
| 4,202,898 A | 5/1980 | Depoortere |
| 4,267,328 A | 5/1981 | Najer et al. |
| 4,333,942 A | 6/1982 | Eistetter et al. |
| 4,415,736 A | 11/1983 | Ciganek et al. |
| 4,485,109 A | 11/1984 | Ciganek et al. |
| 4,504,660 A | 3/1985 | Klaubert et al. |
| 4,699,910 A | 10/1987 | Banholzer et al. |
| 5,462,947 A | 10/1995 | Svensson et al. |
| 5,502,050 A | 3/1996 | Gross |
| 6,057,371 A | 5/2000 | Glennon |
| 6,121,259 A | 9/2000 | Yelle |
| 6,159,979 A | 12/2000 | Gaster et al. |
| 6,175,015 B1 | 1/2001 | Yuan et al. |
| 6,214,859 B1 | 4/2001 | Yoneda et al. |
| 6,903,120 B2 | 6/2005 | Sonesson et al. |
| 6,924,374 B2 | 8/2005 | Sonesson et al. |
| 6,943,177 B2 | 9/2005 | Dwoskin et al. |
| 7,417,043 B2 | 8/2008 | Sonesson et al. |
| 7,579,474 B2 | 8/2009 | Sonesson et al. |
| 7,763,639 B2 | 7/2010 | Sonesson et al. |
| 7,851,629 B2 | 12/2010 | Sonesson et al. |
| 7,923,459 B2 | 4/2011 | Gauthier et al. |
| 8,252,829 B2 | 8/2012 | Duggan |
| 8,501,777 B2 | 8/2013 | Sonesson |
| 9,006,445 B2 | 4/2015 | Sonesson et al. |
| 9,012,476 B2 | 4/2015 | Zimmermann et al. |
| 9,139,525 B2 | 9/2015 | Wikström |
| RE46,117 E | 8/2016 | Sonesson et al. |
| 9,814,706 B2 | 11/2017 | Zimmermann et al. |
| 2003/0109532 A1 | 6/2003 | Sonesson et al. |
| 2007/0238878 A1 | 10/2007 | Desmond et al. |
| 2009/0318500 A1 | 12/2009 | Trewartha et al. |
| 2010/0055133 A1 | 3/2010 | Duffield et al. |
| 2010/0076024 A1 | 3/2010 | Zimmermann et al. |
| 2010/0197712 A1 | 8/2010 | Carlsson et al. |
| 2010/0204258 A1 | 8/2010 | Harris et al. |
| 2011/0206782 A1 | 8/2011 | Zhang |
| 2013/0197031 A1 | 8/2013 | Sonesson |
| 2016/0095847 A1 | 4/2016 | Sonesson |
| 2016/0166559 A1 | 6/2016 | Sonesson |
| 2018/0235950 A1 | 8/2018 | Sonesson |
| 2019/0015401 A1 | 1/2019 | Sonesson |

FOREIGN PATENT DOCUMENTS

EP  0060179 A1  9/1982
EP  0094159 A1  11/1983
(Continued)

OTHER PUBLICATIONS

Over LaVonne Goodman M.D. http://hddrugworks.org/index.php?option=com_content&task=view&id=277 (Year: 2010).*

(Continued)

*Primary Examiner* — Yevgeny Valenrod
(74) *Attorney, Agent, or Firm* — Mark S. Cohen; Pearl Cohen Zedek Latzer Baratz LLP

(57) ABSTRACT

This invention relates to novel pharmaceutical compositions comprising a therapeutically effective combination of a dopaminergic stabilizer known as Pridopidine, and an inhibitor of the vesicular monoamine transporter type 2 (VMAT) known as Tetrabenazine. The pharmaceutical compositions for use according to the invention are contemplated particularly useful for improving the symptomatic therapeutic effects, and for reducing the adverse effects, of Tetrabenazine in the treatment of movement disorders, and in articular movement disorders associated with Huntington's disease, Gilles de la Tourette's syndrome, or tardive dyskinesia.

36 Claims, 16 Drawing Sheets

Specification includes a Sequence Listing.

(56) References Cited

FOREIGN PATENT DOCUMENTS

| | | |
|---|---|---|
| EP | 0369887 A2 | 5/1990 |
| EP | 0533266 A1 | 3/1993 |
| EP | 0533267 A1 | 3/1993 |
| EP | 0533268 A1 | 3/1993 |
| EP | 0675118 A2 | 10/1995 |
| EP | 0867183 A1 | 9/1998 |
| EP | 1419773 A2 | 5/2004 |
| GB | 850662 A | 10/1960 |
| GB | 1060160 A | 3/1967 |
| GB | 1464525 A | 2/1977 |
| GB | 2078746 A | 1/1982 |
| GB | 2083476 A | 3/1982 |
| RU | 2140920 C1 | 11/1999 |
| WO | WO/1989/005799 A1 | 9/1989 |
| WO | WO/1991/009594 A1 | 7/1991 |
| WO | WO/1992/018475 A2 | 10/1992 |
| WO | WO/1993/000313 A2 | 1/1993 |
| WO | WO/1993/004684 A1 | 3/1993 |
| WO | WO/1995/017385 A1 | 6/1995 |
| WO | WO/1995/033729 A1 | 12/1995 |
| WO | WO/1997/003986 A1 | 2/1997 |
| WO | WO/1997/023216 A1 | 7/1997 |
| WO | WO/1998/011068 A1 | 3/1998 |
| WO | WO/1998/047885 A1 | 10/1998 |
| WO | WO/1998/056787 A1 | 12/1998 |
| WO | WO/1999/003470 A1 | 1/1999 |
| WO | WO/2000/003713 A1 | 1/2000 |
| WO | WO/2000/030649 A1 | 6/2000 |
| WO | WO/2000/078728 A1 | 12/2000 |
| WO | WO/2001/046144 A1 | 6/2001 |
| WO | WO/2001/046145 A1 | 6/2001 |
| WO | WO/2001/046146 A1 | 6/2001 |
| WO | WO/2002/005819 A1 | 1/2002 |
| WO | WO/2002/059108 A1 | 8/2002 |
| WO | WO/2003/064393 A1 | 8/2003 |
| WO | WO/2004/099150 A2 | 11/2004 |
| WO | WO/2005/019215 A1 | 3/2005 |
| WO | WO/2005/121087 A1 | 12/2005 |
| WO | WO/2005/121088 A1 | 12/2005 |
| WO | WO/2005/121092 A1 | 12/2005 |
| WO | WO/2006/039325 A2 | 4/2006 |
| WO | WO/2006/040155 A1 | 4/2006 |
| WO | WO/2006/040156 A1 | 4/2006 |
| WO | WO/2007/023141 A1 | 3/2007 |
| WO | WO/2007/042295 A1 | 4/2007 |
| WO | WO/2007/065655 A1 | 6/2007 |
| WO | WO/2007/128694 A1 | 11/2007 |
| WO | WO/2008/127188 A1 | 10/2008 |
| WO | WO/2008/133884 A2 | 11/2008 |
| WO | WO/2008/155357 A2 | 12/2008 |
| WO | WO/2010/057006 A1 | 5/2010 |
| WO | WO/2011/014003 A2 | 2/2011 |
| WO | WO/2011/019956 A2 | 2/2011 |
| WO | WO/2011/107583 A1 | 9/2011 |
| WO | WO/2011/107593 A1 | 9/2011 |
| WO | WO/2011/153157 A2 | 12/2011 |
| WO | WO/2012/002863 A1 | 1/2012 |
| WO | WO/2013/034622 A1 | 3/2013 |
| WO | WO/2013/086425 A1 | 6/2013 |

OTHER PUBLICATIONS

Paula Diana Neuropsychiatric Disease and Treatment 2007:3(5) 545-551. (Year: 2007).*

Clinical Trials https://clinicaltrials.gov/archive/NCT00665223/Feb. 3, 2010 (Year: 2010).*

Altomare, C., Carrupt, P. A., Gaillard, P., El Tayar, N., Testa, B., & Carotti, A. (1992). Quantitative structure-metabolism relationship analyses of MAO-mediated toxication of 1-methyl-4-phenyl-1,2, 3, 6-tetrahydropyridine and analogs. Chemical research in toxicology, 5(3), 366-375.

American Association of Neurological Surgeons (AANS). Movement Disorders (2013). Retrieved on-line at: https://www.aans.org/en/Patients/Neurosurgical-Conditions-and-Treatments/Movement-Disorders.

Andersen, H. L., & Kilpatrick, I. C. (1996). Prevention by (±)-8-hydroxy-2-(di-npropylamino) tetralin of both catalepsy and the rises in rat striatal dopamine metabolism caused by haloperidol. British journal of pharmacology, 118(2), 421-427.

Berberian, D. A., Dennis, E. W., Freele, H. W., Rosi, D., Lewis, T. R., Lorenz, R. R., & Archer, S. (1969). Comparison of schistosomicidal activity of xanthenones and 4-methyl-3-chloroanilines and their hydroxymethyl analogs in Swiss mice and Syrian hamsters infected with Schistosma mansoni. Journal of medicinal chemistry, 12(4), 607-610.

Bickel, M. H. (1969). The pharmacology and biochemistry of N-oxides. Pharmacological Reviews, 21(4), 325-355.

Biobusiness Briefs, Trial watch: NeuroSearch's dopaminergic stabilizer improves movement disorders in Huntington's disease. (Apr. 1, 2010) Nature Reviews Drug Discovery, 9, 260.

Brod, S. A., Lindsey, J. W., & Wolinsky, J. S. (2000). Combination therapy with glatiramer acetate (copolymer-1) and a type I interferon (IFN-α) does not improve experimental autoimmune encephalomyelitis. Annals of neurology, 47(1), 127-131.

Bunney et al., "Schizophrenia and Glutamate", Department of Pharmacology, University of Goteborg, Goteborg, Sweden; Chapter 101, (1995). Retrieved on-line at: http://www.acnp.org/g4/GN401000116/Default.htm.

Burgunder, J. M., Guttman, M., Perlman, S., Goodman, N., van Kammen, D. P., & Goodman, L. (2011). An international survey-based algorithm for the pharmacologic treatment of chorea in Huntington's disease. PLoS currents, 3.

Calligaro, D. O., Fairhurst, J., Hotten, T. M., Moore, N. A., & Tupper, D. E. (1997). The synthesis and biological activity of some known and putative metabolites of the atypical antipsychotic agent olanzapine (LY170053). Bioorganic & Medicinal Chemistry Letters, 7(1), 25-30.

Carlsson, M., & Carlsson, A. (1990). Interactions between glutamatergic and monoaminergic systems within the basal ganglia-implications for schizophrenia and Parkinson's disease. Trends in neurosciences, 13(7), 272-276.

Clinical Trials, Study: NCT00665223 "A Study of Treatment With Pridopidine (ACR16) in Patients With Huntington's Disease (MermaiHD)", (Feb. 3, 2010), Retrieved on-line at: https://clinicaltrials.gov/ct2/history/NCT00665223?V_15=View#StudyPageTop.

Coyle, J. T., Price, D. L., & Delong, M. R. (1983). Alzheimer's disease: a disorder of cortical cholinergic innervation. Science, 219(4589), 1184-1190.

De Yebenes, J. G., Landwehrmeyer, B., Squitieri, F., Reilmann, R., Rosser, A., Barker, R. A., . . . & Tedroff, J. (2011). Pridopidine for the treatment of motor function in patients with Huntington's disease (MermaiHD): a phase 3, randomised, double-blind, placebo-controlled trial. The Lancet Neurology, 10(12), 1049-1057.

Dyhring, T., Nielsen, E. Ø., Sonesson, C., Pettersson, F., Karlsson, J., Svensson, P., . . . & Waters, N. (2010). The dopaminergic stabilizers pridopidine (ACR16) and (−)-OSU6162 display dopamine D2 receptor antagonism and fast receptor dissociation properties. European journal of pharmacology, 628(1-3), 19-26.

Egawa, H., Miyamoto, T., & Matsumoto, J. I. (1986). A new synthesis of 7H-pyrido [1,2, 3-de][1,4] benzoxazine derivatives including an antibacterial agent, ofloxacin. Chemical and pharmaceutical bulletin, 34(10), 4098-4102.

Elslager, E. F., Clarke, J., Werbel, L. M., Worth, D. F., & Davoll, J. (1972). Folate antagonists. 3. 2, 4-diamino-6-(heterocyclic) quina/olines, a novel class of antimetabolites with potent antimalarial and antibacterial activity. Mednl Chem., 15(8), 827-36.

Extended European Search Report for European Patent Application No. EP13772325.0 dated Oct. 15, 2015.

FDA (Jul. 2005) US Department of Health and Human Services, Food and Drug Administration, Centerfor Drug Evaluation and Research, Pharmacology and Toxicology. Guidance for Industry: Estimating the Maximum Safe Starting Dose in Initial Clinical Trials for Therapeutics in Adult Healthy Volunteers. Retrieved on-line at: www.fda.gov/downloads/drugs/guidances/ucm078932.pdf.

(56) References Cited

OTHER PUBLICATIONS

Gessner, W., Brossi, A., Shen, R. S., & Abell, C. W. (1985). Synthesis and dihydropteridine reductase inhibitory effects of potential metabolites of the neurotoxin 1-methyl-4-phenyl-1,2, 3, 6-tetrahydropyridine. Journal of medicinal chemistry, 28(3), 311-317.

Geyer, M. A., & Markou, A. (1995). Animal models of psychiatric disorders. Psychopharmacology: the fourth generation of progress, 787-798.

Goodman L., (Feb. 15, 2010), ACR-16 (Huntexil) Trial Results: Good News from Europe. Retrieved on-line at: http://hddrugworks.org/dr-goodmans-blog/acr-16-huntexil-trial-results-good-news.

Gronier, B., Waters, N., Ponten, H., Klamer, D., Waters, S., & Tedroff, J. (Jun. 2012). [Citation] Pridopidine increases glutamatergic neuron firing in the frontal cortex. In International Congress of Parkinson's Disease and Movement Disorders (vol. 2012).

Grünblatt, E., Mandel, S., & Youdim, M. B. (2000). Neuroprotective Strategies in Parkinson's Disease Using the Models of 6-Hydroxydopamine and MPTP a. Annals of the New York Academy of Sciences, 899(1), 262-273.

Grünblatt, E., Mandel, S., Gassen, M., & Youdim, M. B. H. (1999). Potent neuroprotective and antioxidant activity of apomorphine in MPTP and 6-hydroxydopamine induced neurotoxicity. In Advances in Research on Neurodegeneration (pp. 57-70). Springer, Vienna.

Grundt, P., Prevatt, K. M., Cao, J., Taylor, M., Floresca, C. Z., Choi, J. K., . . . & Newman, A. H. (2007). Heterocyclic analogues of N-(4-(4-(2, 3-dichlorophenyl) piperazin-1-yl) butyl) arylcarboxamides with functionalized linking chains as novel dopamine D3 receptor ligands: potential substance abuse therapeutic agents. Journal of medicinal chemistry, 50(17), 4135-4146.

Guidance for Industry. In Vivo Drug Metabolism/Drug Interaction Studies—Study Design, Data Analysis, and Recommendations for Dosing and Labeling; U.S. Department of Health and Human Services Food and Drug Administration Center for Drug Evaluation and Research (CDER) Center for Biologies Evaluation and Research (CBER) Nov. 1999; Clin/Pharm; Retrieved on-line at: http://home.att.ne.jp/red/akihiro/fda/2635fnl.pdf.

Halmi, K. A., Ackerman, S., Gibbs, J., & Smith, G. (1995). Basic biological overview of eating disorders. Psychopharmacology: the fourth generation of progress. Raven Press, Nueva York, 1609-1615.

Henry, D. W. (1966). A facile synthesis of piperazines from primary amines. Journal of Heterocyclic Chemistry, 3(4), 503-511.

International Search Report and Written Opinion of International Search Authority for PCT Application No. PCT/US2013/035124 dated Jul. 22, 2013.

Jordan, S., Koprivica, V., Dunn, R., Tottori, K., Kikuchi, T., & Altar, C. A. (2004). In vivo effects of aripiprazole on cortical and striatal dopaminergic and serotonergic function. European journal of pharmacology, 483(1), 45-53.

Kalgutkar, A. S., & Nguyen, H. T. (2004). Identification of an N-methyl-4-phenylpyridinium-like metabolite of the antidiarrheal agent loperamide in human liver microsomes: underlying reason (s) for the lack of neurotoxicity despite the bioactivation event. Drug metabolism and disposition, 32(9), 943-952.

Kawashima, T., Okuno, H., Nonaka, M., Adachi-Morishima, A., Kyo, N., Okamura, M., . . . & Bito, H. (2009). Synaptic activity-responsive element in the Arc/Arg3. 1 promoter essential for synapse-to-nucleus signaling in activated neurons. Proceedings of the National Academy of Sciences, 106(1), 316-321.

Klaubert, D. H., Sellstedt, J. H., Guinosso, C. J., Capetola, R. J., & Bell, S. C. (1981). N-(Aminophenyl) oxamic acids and esters as potent, orally active antiallergy agents. Journal of medicinal chemistry, 24(6), 742-748.

Kleinschmidt-Demasters, B. K., & Tyler, K. L. (2005). Progressive multifocal leukoencephalopathy complicating treatment with natalizumab and interferon beta-1a for multiple sclerosis. New England Journal of Medicine, 353(4), 369-374.

Koon, George F.; "Animal Models of Drug Addiction", Department of Neuropharmacology, The Scripps Research Institute, Lo Jolla, California; Chapter 66, (1995). Retrieved on-line at: http://www.acnp.org/g4/GN401000Q72/Default.htm.

Korczyn, Amos D., "Parkinson's Disease", Tel Aviv University, Rama Aviv, Israel; Chapter 126; (1995). Retrieved on-line at: http://www.acnp.org/g4/GN401000142/Default.htm.

Langer-Gould, A., Atlas, S. W., Green, A. J., Bollen, A. W., & Pelletier, D. (2005). Progressive multifocal leukoencephalopathy in a patient treated with natalizumab. New England Journal of Medicine, 353(4), 375-381.

Le Moal, M. I. C. H. E. L., & Simon, H. (1991). Mesocorticolimbic dopaminergic network: functional and regulatory roles. Physiological reviews, 71(1), 155-234.

Manoury, P. M., Dumas, A. P., Najer, H., Branceni, D., Prouteau, M., & Lefevre-Borg, F. M. (1979). Synthesis and analgesic activities of some (4-substituted phenyl-1-piperazinyl) alkyl 2-aminobenzoates and 2-aminonicotinates. Journal of medicinal chemistry, 22(5), 554-559.

Morita, S., Kitano, K., Matsubara, J., Ohtani, T., Kawano, Y., Otsubo, K., & Uchida, M. (1998). Practical application of the palladium-catalyzed amination in phenylpiperazine synthesis: An efficient synthesis of a metabolite of the antipsychotic agent aripiprazole. Tetrahedron, 54(19), 4811-4818.

Nacci, V. (1973). Antiblastic Substances. LII. Tylophorine Analogs. 1. Synthesis and Cytostiic and Cytoxic Activity of 4-(3, 4-dimethoxyphenyl) piperdine. Farmaco, Edizione Scientifica, 328(5), 399-419.

Natesan, S., Svensson, K. A., Reckless, G. E., Nobrega, J. N., Barlow, K. B., Johansson, A. M., & Kapur, S. (2006). The dopamine stabilizers (S)-(−)-(3-methanesulfonyl-phenyl)-1-propyl-piperidine [(−)-OSU6162]and 4-(3-methanesulfonylphenyl)-1-propyl-piperidine (ACR16) show high in vivo D2 receptor occupancy, antipsychotic-like efficacy, and low potential for motor side effects in the rat. Journal of Pharmacology and Experimental Therapeutics, 318(2), 810-818.

Nilsson, M., Carlsson, A., Markinhuhta, K. R., Sonesson, C., Pettersson, F., Gullme, M., & Carlsson, M. L. (2004). The dopaminergic stabiliser ACR16 counteracts the behavioural primitivization induced by the NMDA receptor antagonist MK-801 in mice: implications for cognition. Progress in Neuro-Psychopharmacology and Biological Psychiatry, 28(4), 677-685.

Oshiro, Y., Sato, S., Kurahashi, N., Tanaka, T., Kikuchi, T., Tottori, K., . . . & Nishi, T. (1998). Novel antipsychotic agents with dopamine autoreceptor agonist properties: synthesis and pharmacology of 7-[4-(4-phenyl-1-piperazinyl) butoxy]-3, 4-dihydro-2 (1 H)-quinolinone derivatives. Journal of medicinal chemistry, 41(5), 658-667.

Paleacu, D. (2007). Tetrabenazine in the treatment of Huntington's disease. Neuropsychiatric disease and treatment, 3(5), 545.

Pettersson, F., Pontén, H., Waters, N., Waters, S., & Sonesson, C. (2010). Synthesis and evaluation of a set of 4-phenylpiperidines and 4-phenylpiperazines as D2 receptor ligands and the discovery of the dopaminergic stabilizer 4-[3-(methylsulfonyl) phenyl]-1-propylpiperidine (huntexil, pridopidine, ACR16). Journal of medicinal chemistry, 53(6), 2510-2520.

Pochon, S. (2011). 63rd Annual Meeting of the American Academy of Neurology.

Ponten, H., Kullingsjö, J., Lagerkvist, S., Martin, P., Pettersson, F., Sonesson, C., . . . & Waters, N. (2010). In vivo pharmacology of the dopaminergic stabilizer pridopidine. European journal of pharmacology, 644(1-3), 88-95.

Ponten, H., Sönniksen, K., Abrahamsson, T., Waters, N., Gustafsson, B., Hanse, E., & Groc, L. (2005). Behavioral and neurochemical repercussions of hippocampal network activity blockade during the neonatal period. Developmental brain research, 155(1), 81-86.

Radl, S., Hezký, P., Taimr, J., Proška, J., & Krejčí, I. (1999). Synthesis of piperidine analogs of 1-(3-chlorophenyl) piperazine, a well known serotonin ligand. Journal of heterocyclic chemistry, 36(4), 1017-1022.

(56) References Cited

OTHER PUBLICATIONS

Rajšner, M., Kopicová, Z., Holubek, J., Svátek, E., Metyš, J., Bartošová, M., . . . & Protiva, M. (1978). 4, 4-Bis (4-fluorophenyl) butylamines and their cyclic analogues; An efficient synthesis of the neuroleptic penfluridol. Collection of Czechoslovak Chemical Communications, 43(7), 1760-1777.

Reches, A. V. I. N. O. A. M., Burke, R. E., Kuhn, C. M., Hassan, M. N., Jackson, V. R., & Fahn, S. T. A. N. L. E. Y. (1983). Tetrabenazine, an amine-depleting drug, also blocks dopamine receptors in rat brain. Journal of Pharmacology and Experimental Therapeutics, 225(3), 515-521.

Roffler-Tarlov, S. U. Z. A. N. N. E., Sharman, D. F., & Tegerdine, P. (1971). 3, 4-Dihydroxyphenylacetic acid and 4-hydroxy-3-methoxyphenylacetic acid in the mouse striatum: a reflection of intra-and extra-neuronal metabolism of dopamine?. British journal of pharmacology, 42(3), 343-351.

Rosenfeld, J., Kawai, M., Rigg, J. R. A., & Khandelwal, J. K. (1976). Gas chromatographic method for the analysis of butyrophenones based on the Hofmann degradation reaction. Journal of Chromatography A, 129, 387-392.

Roth et al., "Biochemical Pharmacology of Midbrain Dopamine Neurons"; Chapter 21; Yale University of Medicine; New Haven, CT; (1995); Retrieved on-line at: http://www.acnp.org/g4/GN401000Q21/Default.htm.

Sato, K., Hyodo, M., Aoki, M., Zheng, X. Q., & Noyori, R. (2001). Oxidation of sulfides to sulfoxides and sulfones with 30% hydrogen peroxide under organic solvent-and halogen-free conditions. Tetrahedron, 57(13), 2469-2476.

Satou, T., Anderson, A. J., Itoh, T., Tamai, Y., Hayashi, Y., & Hashimoto, S. (2001). Repetitive administration of tetrabenazine induces irreversible changes in locomotion and morphology of the substantia nigra in rats. Experimental and Toxicologic Pathology, 53(4), 303-308.

Schaefer, G. J., & Michael, R. P. (1984). Drug interactions on spontaneous locomotor activity in rats: Neuroleptics and amphetamine-induced hyperactivity. Neuropharmacology, 23(8), 909-914.

Seeraan, Philip "Dopamine Receptors Clinical Correlates"; Departmants of Pharmacology and Psychiatry, University of Toronto, Toronto, Ontario, Canada; Chapter 26, (1995). Retrieved on-line at: http://www.acnp.org/g4/GN401000Q27/Default.htm.

Self, D. P., West, D. E., & Stillings, M. R. (1980). cine and tele Substitutions in the reaction of 2, 3-dinitroaniline with secondary amines. Journal of the Chemical Society, Chemical Communications, (6), 281-282.

Shannon, K. M., & Fraint, A. (2015). Therapeutic advances in Huntington's disease. Movement Disorders, 30(11), 1539-1546.

Smaill, J. B., Fan, J. Y., Papa, P. V., O'Connor, C. J., & Denny, W. A. (1998). Mono-and difunctional nitrogen mustard analogues of the DNA minor groove binder pibenzimol. Synthesis, cytotoxicity and interaction with DNA. Anti-cancer drug design, 13(3), 221-242.

Sonesson, C., Lin, C. H., Hansson, L., Waters, N., Svensson, K., Carlsson, A., . . . & Wikstroem, H. (1994). Substituted (S)-phenylpiperidines and rigid congeners as preferential dopamine autoreceptor antagonists: synthesis and structure-activity relationships. Journal of medicinal chemistry, 37(17), 2735-2753.

Steward, O., & Worley, P. F. (2001). Selective targeting of newly synthesized Arc mRNA to active synapses requires NMDA receptor activation. Neuron, 30(1), 227-240.

Strange, P. G. (2001). Antipsychotic drugs: importance of dopamine receptors for mechanisms of therapeutic actions and side effects. Pharmacological reviews, 53(1), 119-134.

Takai, H., Obase, H., & Teranishi, M. (1986). Reaction of Spiro [4H-3, 1-benzoxazine-4, 4'-piperidin]-2 (1H)-one Derivatives and Related Compounds with Phosphorus Oxychloride. Chemical and pharmaceutical bulletin, 34(5), 1901-1906.

Vollmer, T., Panitch, H., Bar-Or, A., Dunn, J., Freedman, M. S., Gazda, S. K., . . . & Arnold, D. L. (2008). Glatiramer acetate after induction therapy with mitoxantrone in relapsing multiple sclerosis. Multiple Sclerosis Journal, 14(5), 663-670.

Waters, S., Pettersson, F., Dyhring, T., Sonesson, C., Tedroff, J., Waters, N., & Pontén, H. (2010). Poster 23: Pharmacology of the Dopaminergic Stabilizer Pridopidine (ACR16). Neurotherapeutics, 7(1), 145-146.

Weber, E., Sonders, M., Quarum, M., McLean, S., Pou, S., & Keana, J. F. (1986). 1, 3-Di (2-[5-3H] tolyl) guanidine: a selective ligand that labels sigma-type receptors for psychotomimetic opiates and antipsychotic drugs. Proceedings of the National Academy of Sciences, 83(22), 8784-8788.

Willner, Paul; "Dopaminergic Mechanisms in Depression and Mania"; Department of Psychology, University College of Swansea, Wales, United Kingdom; Chapter 80; (1995). Retrieved on-line at: http://www.acnp.org/g4/GN401000Q93/Default.htm.

XENAZINE (Tetrabenzine), FDA Label, (2017) Retrieved on-line at: https://www.accessdata.fda.gov/drugsatfda_docs/label/2017/021894s013lbl.pdf.

Zimmermann, A., Frøstrup, B., & Bond, A. D. (2012). Polymorphs of pridopidine hydrochloride. Crystal Growth & Design, 12(6), 2961-2968.

Dunlop, Boadie W.; Nemeroff, Charles B. The role of dopamine in the pathophysiology of depression. Archives of general psychiatry, 2007, 64.3: 327-337.

Garcia-Miralles, Marta, et al. Early pridopidine treatment improves behavioral and transcriptional deficits in YAC128 Huntington disease mice. JCI insight, 2017, 2.23.

Kaur, Navneet, et al. Tetrabenazine: spotlight on drug review. Annals of Neurosciences, 2016, 23.3: 176-185.

Bramham, Clive R., et al. The Arc of synaptic memory. Experimental brain research, 2010, 200.2: 125-140.

Covington, Herbert E., et al. Antidepressant effect of optogenetic stimulation of the medial prefrontal cortex, Journal of Neuroscience, 2010, 30.48: 16082-16090.

Huntington Study Group, et al. Tetrabenazine as antichorea therapy in Huntington disease: a randomized controlled trial. Neurology, 2006, 66.3: 366-372.

Kobayashi, Koji, et al. The assessment of mouse spontaneous locomotor activity using motion picture. Journal of pharmacological sciences, 2020, 143.2: 83-88.

Pei Q., et al. Antidepressant drug treatment induces Arc gene expression in the rat brain. Neuroscience, 2003, 121.4: 975-982.

Taoufik, Era, et al. Synaptic dysfunction in neurodegenerative and neurodevelopmental diseases: an overview of induced pluripotent stem-cell-based disease models. Open biology, 2018, 8.9: 180138.

Thomas, Charles; Marcaletti, Stefan; Feige, Jérôme N. Assessment of spontaneous locomotor and running activity in mice. Current protocols in mouse biology, 2011, 1.1: 185-198.

Waters, Susanna, et al. Co-administration of the dopaminergic stabilizer pridopidine and tetrabenazine in rats. Journal of Huntington's disease, 2014, 3.3: 285-298.

* cited by examiner

PHARMACEUTICAL COMPOSITIONS FOR COMBINATION THERAPY

CROSS-REFERENCE TO RELATED APPLICATIONS

This application is a continuation of U.S. Ser. No. 16/054,054, filed Aug. 3, 2018, which is a continuation of U.S. Ser. No. 15/612,779, filed Jun. 2, 2017, which is a continuation of U.S. Ser. No. 13/856,254, filed Apr. 3, 2013 which claims the benefit of U.S. Provisional Application No. 61/783,730, filed Mar. 14, 2013, U.S. Provisional Application No. 61/625,192, filed Apr. 17, 2012, and U.S. Provisional Application No. 61/620,203, filed Apr. 4, 2012, the entire contents of which are hereby incorporated by reference herein.

Throughout this application, various publications are referred to, and disclosures of these publications cited in their entireties are hereby incorporated by reference into this application in order to more fully describe the state of the art as of the date of the invention described herein.

SEQUENCE LISTING STATEMENT

The instant application contains a Sequence Listing which has been submitted electronically in ASCII format and is hereby incorporated by reference in its entirety. Said ASCII copy, created on Sep. 9, 2019, is named P-587446-US3-SQL-ST25-09SEP19.txt and is 4 KB in size.

BACKGROUND OF THE INVENTION

Pridopidine, i.e. 4-(3-Methanesulfonyl-phenyl)-1-propyl-piperidine, is a drug substance currently in clinical development for the treatment of Huntington's disease. This compound was first described in WO 01/46145.

Pridopidine is a dopaminergic stabilizer that displays competitive dopamine D2 receptor antagonism with fast dissociation kinetics (Dyhring, 2010). In vivo Pridopidine increases turnover and release of dopamine in the striatum and in the frontal cortex (Poten, 2010; Pettersson 2010). Behavioural effects include antagonism of psychostimulant induced hyperactivity, suggesting antipsychotic properties, but no inhibitory effects on spontaneous locomotor activity (Ponten, 2010; Natesan 2006; Nilsson, 2004).

Tetrabenzine, i.e. (SS,RR)-3-Isobutyl-9,10-dimethoxy-1,3,4,6,7,11b-hexahydro-pyrido[2,1-a]isoquinolin-2-one, is a drug substance marketed for the symptomatic treatment of certain movement disorders (FDA Label for XENAZINE (Tetrabenzine) 07/06/2011). Tetrabenazine, is an inhibitor of the vesicular monoamine transporter type 2 (VMAT), that blocks the vesicular storage of monoamine neurotransmitters in the brain, thereby leading to reduced synaptic release of dopamine, serotonin and norepinephrin (Paleacu, 2007). This reduction of monoaminergic neurotransmission is associated with suppression of e.g. dopamine dependent functions, including movement and reward. The suppression of movements is used therapeutically to ameliorate involuntary movements in e.g. Huntington's disease, tardive dyskinesia, and Tourette's disease. However, treatment with Tetrabenazine is associated with severe side effects. Such side effects include parkinsonism, i.e. rigidity and impaired motor function, depression, and impaired functional capacity.

Involuntary movements such as chorea and dyskinesia, occurring as part of the clinical manifestations of e.g. Huntington's disease, are believed to be related to impaired activity in the indirect cortico-striato-thalamic pathway. Hence, the beneficial effects of Tetrabenazine on such involuntary movements are due to a decreased tone at dopamine D2 receptors on medium spiny neurons of the indirect pathway, occurring as a consequence of the reduction in dopamine transmission engendered by Tetrabenazine. The decreased dopamine D2 receptor tone leads to a reduced inhibition of these medium spiny neurons, and therefore, an increased activity of the indirect pathway, and improved suppression of involuntary movements. Accordingly, dopamine D2 antagonists are also frequently used to alleviate chorea in HD (Steward 2001).

Combination Therapy

The administration of two drugs to treat a given condition, such as a movement disorder, raises a number of potential problems. In vivo interactions between two drugs are complex. The effects of any single drug are related to its absorption, distribution, and elimination. When two drugs are introduced into the body, each drug can affect the absorption, distribution, and elimination of the other and hence, alter the effects of the other. For instance, one drug may inhibit, activate or induce the production of enzymes involved in a metabolic route of elimination of the other drug (Guidance for Industry, 1999). In one example, combined administration of GA and interferon (IFN) has been experimentally shown to abrogate the clinical effectiveness of either therapy. (Brod 2000) In another experiment, it was reported that the addition of prednisone in combination therapy with IFN-β antagonized its up-regulator effect. Thus, when two drugs are administered to treat the same condition, it is unpredictable whether each will complement, have no effect on, or interfere with, the therapeutic activity of the other in a human subject.

Not only may the interaction between two drugs affect the intended therapeutic activity of each drug, but the interaction may increase the levels of toxic metabolites (Guidance for Industry, 1999). The interaction may also heighten or lessen the side effects of each drug. Hence, upon administration of two drugs to treat a disease, it is unpredictable what change will occur in the negative side profile of each drug. In one example, the combination of natalizumab and interferon β-1a was observed to increase the risk of unanticipated side effects. (Vollmer, 2008; Rudick 2006; Kleinschmidt-DeMasters, 2005; Langer-Gould 2005)

Additionally, it is difficult to accurately predict when the effects of the interaction between the two drugs will become manifest. For example, metabolic interactions between drugs may become apparent upon the initial administration of the second drug, after the two have reached a steady-state concentration or upon discontinuation of one of the drugs (Guidance for Industry, 1999).

Therefore, the state of the art at the time of filing is that the effects of combination therapy of two drugs, in particular Pridopidine and Tetrabenazine, cannot be predicted until the results of combination studies are available.

BRIEF SUMMARY OF THE INVENTION

It has now surprisingly been found that Pridopidine is capable of reversing the behavioural inhibition caused by Tetrabenazine, while maintaining the primary pharmacological effect of Pridopidine, i.e. dopamine D2 receptor blockade. These findings suggest that coadministration of Pridopidine and Tetrabenazine would improve the therapeutically beneficial effects of Tetrabenazine, i.e. further alleviate involuntary movements, as well as reduced the adverse motor and affective effects.

The subject invention provides a method of treating a subject afflicted with a movement disorder comprising periodically administering to the subject an amount of Tetrabenazine or a pharmaceutically acceptable salt thereof, and an amount of Pridopidine or a pharmaceutically acceptable salt thereof.

The subject invention also provides a method of treating a subject afflicted with obesity, an obesity associated disorder, or a cardiovascular side effect of Pridopidine comprising administering to the subject an amount of Pridopidine or a pharmaceutically acceptable salt thereof, and an amount of Tetrabenazine or a pharmaceutically acceptable salt thereof.

The subject invention also provides a method of reducing or preventing one or more side effects of periodically administering of an amount of Tetrabenazine or a pharmaceutically acceptable salt thereof to a subject, comprising periodically administering to the subject an amount of Pridopidine or a pharmaceutically acceptable salt thereof.

The subject invention also provides a package comprising:
 a) a first pharmaceutical composition comprising an amount of Tetrabenazine or a pharmaceutically ac-ceptable salt thereof and a pharmaceutically ac-ceptable carrier;
 b) a second pharmaceutical composition comprising and amount of Pridopidine or pharmaceutical acceptable salt thereof and a pharmaceutically acceptable carrier; and
 c) instruction for use for the first and the second pharmaceutical compositions together to treat a subject afflicted a movement disorder.

The subject invention also provides Pridopidine or pharmaceutically acceptable salt thereof for use as an add-on therapy of or in combination with Tetrabenazine or pharmaceutical acceptable salt thereof in treating a subject afflicted with a movement disorder.

The subject invention also provides a pharmaceutical composition comprising an amount of Tetrabenazine or pharmaceutically acceptable salt thereof, an amount of Pridopidine or pharmaceutical acceptable salt thereof, and at least one pharmaceutical acceptable carrier.

The subject invention also provides the use of:
 a) an amount of Tetrabenazine or pharmaceutically acceptable salt thereof; and
 b) an amount of Pridopidine or pharmaceutically acceptable salt thereof
in the preparation of a combination for treating a subject afflicted with a movement disorder wherein the amount of Tetrabenazine or pharmaceutically acceptable salt thereof and the amount of Pridopidine or pharmaceutically acceptable salt thereof are administered simultaneously or contemporaneously.

The subject invention also provides a pharmaceutical composition comprising an amount of Tetrabenazine or a pharmaceutically acceptable salt thereof for use in treating a subject afflicted with a movement disorder, in combination with an amount of Pridopidine or pharmaceutically acceptable salt thereof, by periodically administering to the subject the pharmaceutical composition and the amount of Pridopidine or pharmaceutically acceptable salt thereof.

The subject invention also provides a pharmaceutical composition comprising an amount of Pridopidine or pharmaceutically acceptable salt thereof for use treating a subject afflicted with a movement disorder, in combination with an amount of Tetrabenazine or a pharmaceutically acceptable salt thereof, by periodically administering to the subject the pharmaceutical composition and the amount of Tetrabenazine or a pharmaceutically acceptable salt thereof.

The subject invention also provides Tetrabenazine or a pharmaceutically acceptable salt thereof and Pridopidine or a pharmaceutically acceptable salt thereof for the treatment of a subject afflicted with a movement disorder, wherein the Tetrabenazine or a pharmaceutically acceptable salt thereof and the Pridopidine or a pharmaceutically acceptable salt thereof are administered simultaneously, separately or sequentially.

The subject invention also provides a product containing an amount of Tetrabenazine or a pharmaceutically acceptable salt thereof and an amount of Pridopidine or a pharmaceutically acceptable salt thereof for simultaneous, separate or sequential use in treating a subject afflicted with a movement disorder.

The subject invention also provides a method of treating a subject afflicted with obesity, an obesity associated disorder or a cardiovascular side effect of Pridopidine comprising administering to the subject a combination of a therapeutically effective amount of Pridopidine or a pharmaceutically acceptable salt thereof, and a therapeutically effective amount of Tetrabenazine or a pharmaceutically acceptable salt thereof, wherein the amounts when taken together are effective to treat the subject.

The subject invention also provides a combination of Pridopidine, or a pharmaceutically acceptable salt thereof; and Tetrabenazine, or a pharmaceutically acceptable salt thereof; for the treatment, prevention or alleviation of obesity, or an obesity associated disorder, and for treatment, prevention or alleviation of the cardiovascular side effects of Pridopidine, in a mammal, including a human.

In another aspect, the invention provides a combination of Pridopidine, or a pharmaceutically acceptable salt thereof, and Tetrabenazine, or a pharmaceutically acceptable salt thereof, for use as a medicament for the treatment, prevention or alleviation of a movement disorder.

In another aspect the invention provides a combination of Pridopidine, or a pharmaceutically acceptable salt thereof, and Tetrabenazine, or a pharmaceutically acceptable salt thereof, for use as a medicament.

In another aspect the invention provides a combination of Pridopidine, or a pharmaceutically acceptable salt thereof; and Tetrabenazine, or a pharmaceutically acceptable salt thereof; for the treatment, prevention or alleviation of obesity, or an obesity associated disorder, and for treatment, prevention or alleviation of the cardiovascular side effects of Pridopidine, in a mammal, including a human.

In another aspect the invention relates to the use of a combination of Pridopidine, or a pharmaceutically acceptable salt thereof; and Tetrabenazine, or a pharmaceutically acceptable salt thereof; for the manufacture of a medicament for the treatment, prevention or alleviation of a movement disorder of a mammal, including a human.

In another aspect the invention provides a pharmaceutical composition comprising Pridopidine, or a pharmaceutically acceptable salt thereof, for use in a combination therapy together with a pharmaceutical composition comprising Tetrabenazine, or a pharmaceutically acceptable salt thereof, for the treatment, prevention or alleviation of a movement disorder.

In another aspect the invention provides a pharmaceutical composition comprising a therapeutically effective amount of Pridopidine, or a pharmaceutically acceptable salt thereof, and a therapeutically effective amount of Tetrabenazine, or a pharmaceutically acceptable salt thereof, together with one or more adjuvants, excipients, carriers and/or diluents.

In another aspect the invention provides a method of treatment, prevention or alleviation of a movement disorder in a living animal body, including a human, which method comprises the step of administering to such a living animal body in need thereof, a therapeutically effective amount of Pridopidine, or a pharmaceutically acceptable salt thereof; in a combination therapy with Tetrabenazine, or a pharmaceutically acceptable salt thereof.

In another aspect the invention provides a kit of parts comprising at least two separate unit dosage forms (A) and (B), wherein (A) comprises Pridopidine, or a pharmaceutically acceptable salt thereof; and (B) comprises Tetrabenazine, or a pharmaceutically acceptable salt thereof; and optionally (C) instructions for the simultaneous, sequential or separate administration of the Pridopidine of (A) and the Tetrabenazine of (B), to a patient in need thereof.

In another aspect the invention provides an article of manufacture, comprising (A) a first pharmaceutical dosage form comprising Pridopidine, or a pharmaceutically acceptable salt thereof; and (B) a second pharmaceutical dosage form comprising Tetrabenazine, or a pharmaceutically acceptable salt thereof; wherein the article contains first and second pharmaceutical dosage forms.

In another aspect the invention provides a method of treating a subject afflicted with a movement disorder comprising administering to the subject a combination of a therapeutically effective amount of Pridopidine or a pharmaceutically acceptable salt thereof, and a therapeutically effective amount of Tetrabenazine or a pharmaceutically acceptable salt thereof, wherein the amounts when taken together are effective to treat the human patient.

In another aspect the invention provides a method of treating a mammal, including a human, afflicted with an obesity, or an obesity associated disorder or of the cardiovascular side effects of Pridopidine comprising administering to the subject a combination of a therapeutically effective amount of Pridopidine or a pharmaceutically acceptable salt thereof, and a therapeutically effective amount of Tetrabenazine or a pharmaceutically acceptable salt thereof, wherein the amounts when taken together are effective to treat the mammal.

Other objects of the invention will be apparent to the person skilled in the art from the following detailed description and examples.

BRIEF DESCRIPTION OF THE SEVERAL VIEWS OF THE DRAWINGS

The present invention is further illustrated by reference to the accompanying drawings.

DETAILED DESCRIPTION OF THE INVENTION

Figure 1:
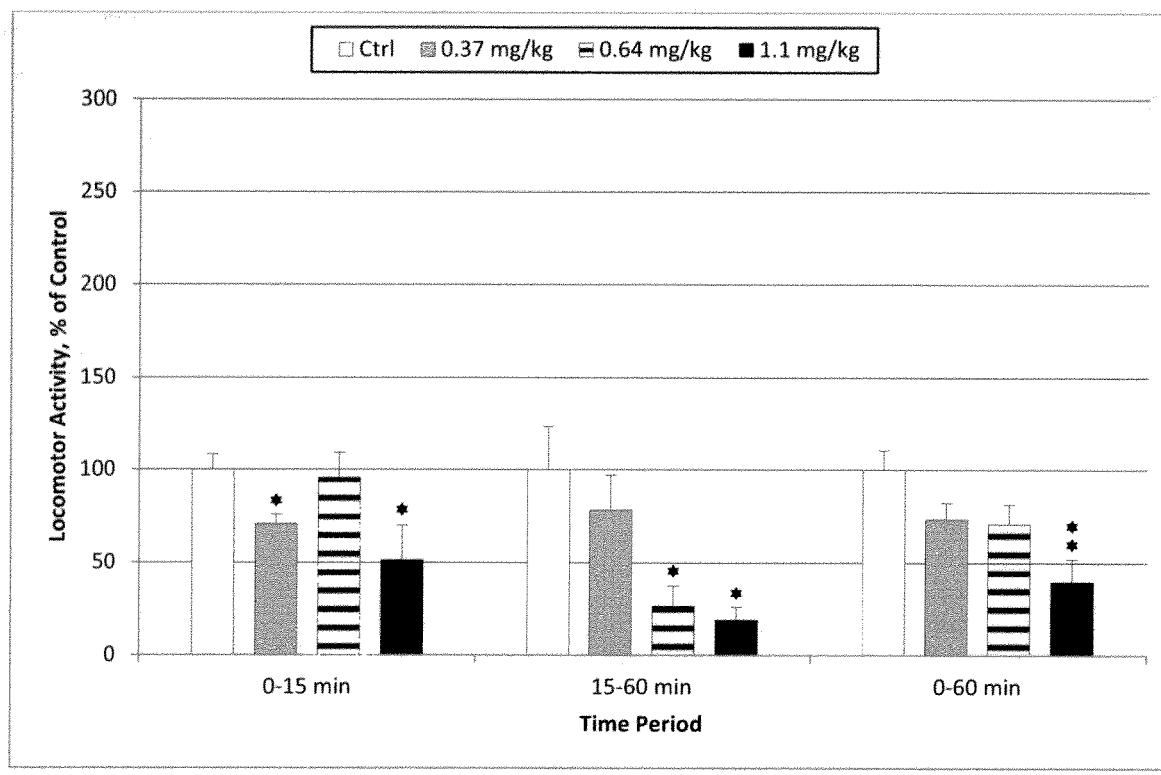
FIG. 1. Spontaneous locomotor activity (LMA) expressed as a percentage of the mean control group value for Tetrabenazine. Activity is shown by dose for each recorded time period. Animals were allocated into four different treatment groups, n=5. The treatment groups consisted of Vehicle (Glucose 5.5% v/w) and Tetrabenazine tested at three doses (0.37; 0.64 and 1.1 μmol/kg). All compounds were injected s.c. four minutes before start of locomotor activity recording at a volume of 5 ml/kg.

The present invention relates to a combination therapy using Pridopidine and Tetrabenazine for the treatment, prevention or alleviation of a movement disorder.

The effects of Pridopidine when given in combination with Tetrabenazine suggest, firstly, that the primary pharmacological effect of Pridopidine, i.e. dopamine D2 receptor blockade, is still present under coadministration with Tetrabenazine. This is reflected by the additional increase in striatal DOPAC induced by Pridopidine in Tetrabenazine treated rats. Given that a reduced tone at striatal D2 receptors is the proposed mechanism by which Tetrabenazine can alleviate involuntary movements in e.g. Huntington's disease, Tourettes disorder and tardive dyskinesia, this suggests that combining Tetrabenazine with Pridopidine could give additional clinical benefit in these disorders.

Secondly, Pridopidine reversed the behavioural inhibition caused by Tetrabenazine. This behavioural inhibition is a preclinical correlate of some troublesome dopamine related side effects limiting the use of Tetrabenazine, especially the clear-cut motor side effects, such as parkinsonism, i.e. reduced motility, but also possibly depressed mood. It should be noted that this reversal of the behavioural inhibition induced by Tetrabenazine is not to be expected from a compound acting as a pure antagonist at dopamine D2 receptors, such as Pridopidine, and was not observed in a similar study performed with the dopamine D2 antagonist Haloperidol. Rather, co-treatment with Haloperidol further reduced locomotor activity.

Hence, these preclinical behavioural data implies that Pridopidine might counteract the adverse motor and affective effects of Tetrabenazine.

The subject invention provides a method of treating a subject afflicted with a movement disorder comprising periodically administering to the subject an amount of Tetrabenazine or a pharmaceutically acceptable salt thereof, and an amount of Pridopidine or a pharmaceutically acceptable salt thereof.

The subject invention also provides a method of treating a subject afflicted with obesity, an obesity associated disorder, or a cardiovascular side effect of Pridopidine comprising administering to the subject an amount of Pridopidine or a pharmaceutically acceptable salt thereof, and an amount of Tetrabenazine or a pharmaceutically acceptable salt thereof.

In an embodiment, the amounts when taken together are more effective to treat the subject than when each agent at the same amount is administered alone.

In an embodiment, either the amount of Tetrabenazine or a pharmaceutically acceptable salt thereof when taken alone, and the amount of Pridopidine or a pharmaceutically acceptable salt thereof when taken alone, or each such amount when taken alone is not effective to treat the subject.

The subject invention also provides a method of reducing or preventing one or more side effects of periodically administering of an amount of Tetrabenazine or a pharmaceutically acceptable salt thereof to a subject, comprising periodically administering to the subject an amount of Pridopidine or a pharmaceutically acceptable salt thereof.

In an embodiment, the one or more side effects are selected from depression, suicidality, akathisia, restlessness, agitation, parkinsonism, sedation, somnolence, and dysphagia.

In an embodiment, the side effect is parkinsonism.

In an embodiment, the subject is afflicted with a movement disorder.

In an embodiment, the amount of Tetrabenazine or a pharmaceutically acceptable salt thereof is administered via oral administration.

In an embodiment, the amount of Tetrabenazine or a pharmaceutically acceptable salt thereof is administered daily.

In an embodiment, the amount of Tetrabenazine or a pharmaceutically acceptable salt thereof is administered twice daily.

In an embodiment, the amount of Tetrabenazine or a pharmaceutically acceptable salt thereof is administered three times daily.

In an embodiment, the amount of Tetrabenazine or a pharmaceutically acceptable salt thereof is 0.05 mg/kg per day to 0.20 mg/kg per day.

In an embodiment, the amount of Tetrabenazine or a pharmaceutically acceptable salt thereof is 5-100 mg/day.

In an embodiment, the amount of Tetrabenazine or a pharmaceutically acceptable salt thereof is 12.5 mg/day, 25 mg/day, 37.5 mg/day, 50 mg/day, 75 mg/day, or 100 mg/day.

In an embodiment, the amount of Pridopidine or a pharmaceutically acceptable salt thereof is administered via oral administration.

In an embodiment, the amount of Pridopidine or a pharmaceutically acceptable salt thereof is administered daily.

In an embodiment, the amount of Pridopidine or a pharmaceutically acceptable salt thereof is administered twice daily.

In an embodiment, the amount of Pridopidine or a pharmaceutically acceptable salt thereof is 1.5 µmol/kg per day to 20 µmol/kg per day.

In an embodiment, the amount of Pridopidine or a pharmaceutically acceptable salt thereof is 10-100 mg/day.

In an embodiment, the amount of Pridopidine or a pharmaceutically acceptable salt thereof is 10 mg/day, 20 mg/day, 22.5 mg/day, 45 mg/day, or 90 mg/day.

In an embodiment, the movement disorder is Huntington's disease, Tourette's syndrome, or tardive dyskinesia.

In an embodiment, the amount of Tetrabenazine or a pharmaceutically acceptable salt thereof and the amount of Pridopidine or a pharmaceutically acceptable salt thereof is effective to alleviate a symptom of the movement disorder.

In an embodiment, the symptom is chorea.

In an embodiment, the subject is receiving Tetrabenazine therapy prior to initiating administration of Pridopidine or a pharmaceutically acceptable salt thereof.

In an embodiment, the amount of Tetrabenazine or a pharmaceutically acceptable salt thereof and the amount of Pridopidine or a pharmaceutically acceptable salt thereof are administered simultaneously.

In an embodiment, the subject is a human patient.

The subject invention also provides a package comprising:

a) a first pharmaceutical composition comprising an amount of Tetrabenazine or a pharmaceutically acceptable salt thereof and a pharmaceutically acceptable carrier;

b) a second pharmaceutical composition comprising and amount of Pridopidine or pharmaceutical acceptable salt thereof and a pharmaceutically acceptable carrier; and c) instruction for use for the first and the second pharmaceutical compositions together to treat a subject afflicted a movement disorder.

In an embodiment, the package is for use in treating a subject afflicted with a movement disorder.

In an embodiment, the movement disorder is Huntington's disease, Tourette's syndrome, or tardive dyskinesia.

The subject invention also provides Pridopidine or pharmaceutically acceptable salt thereof for use as an add-on therapy of or in combination with Tetrabenazine or pharmaceutical acceptable salt thereof in treating a subject afflicted with a movement disorder.

In an embodiment, the movement disorder is Huntington's disease, Tourette's syndrome, or tardive dyskinesia.

The subject invention also provides a pharmaceutical composition comprising an amount of Tetrabenazine or pharmaceutically acceptable salt thereof, an amount of Pridopidine or pharmaceutical acceptable salt thereof, and at least one pharmaceutical acceptable carrier.

In an embodiment, the amount of Tetrabenazine or pharmaceutically acceptable salt thereof is 5-100 mg.

In an embodiment, the amount of Tetrabenazine or pharmaceutically acceptable salt thereof is 5 mg, 6.25 mg, 12.5 mg, 25 mg, 37.5 mg, 50 mg, 75 mg, or 100 mg.

In an embodiment, the amount of Pridopidine or pharmaceutical acceptable salt thereof is 10-100 mg.

In an embodiment, the amount of Pridopidine or pharmaceutical acceptable salt thereof is 10 mg, 22.5 mg, 45 mg, or 90 mg.

In an embodiment, the pharmaceutical composition is for use in treating a subject afflicted with a movement disorder.

In an embodiment, the movement disorder is Huntington's disease, Tourette's syndrome, or tardive dyskinesia.

In an embodiment, the pharmaceutical composition is for use in treating, preventing or alleviating a subject afflicted with obesity, an obesity associated disorder, or a cardiovascular side effects of Pridopidine.

The subject invention also provides the use of:

a) an amount of Tetrabenazine or pharmaceutically acceptable salt thereof; and b) an amount of Pridopidine or pharmaceutically acceptable salt thereof in the preparation of a combination for treating a subject afflicted with a movement disorder wherein the amount of Tetrabenazine or pharmaceutically acceptable salt thereof and the amount of Pridopidine or pharmaceutically acceptable salt thereof are administered simultaneously or contemporaneously.

In an embodiment, the movement disorder is Huntington's disease, Tourette's syndrome, or tardive dyskinesia.

The subject invention also provides a pharmaceutical composition comprising an amount of Tetrabenazine or a pharmaceutically acceptable salt thereof for use in treating a subject afflicted with a movement disorder, in combination with an amount of Pridopidine or pharmaceutically acceptable salt thereof, by periodically administering to the subject the pharmaceutical composition and the amount of Pridopidine or pharmaceutically acceptable salt thereof.

The subject invention also provides a pharmaceutical composition comprising an amount of Pridopidine or pharmaceutically acceptable salt thereof for use treating a subject afflicted with a movement disorder, in combination with an amount of Tetrabenazine or a pharmaceutically acceptable salt thereof, by periodically administering to the subject the pharmaceutical composition and the amount of Tetrabenazine or a pharmaceutically acceptable salt thereof.

In an embodiment, the movement disorder is Huntington's disease, Tourette's syndrome, or tardive dyskinesia.

The subject invention also provides Tetrabenazine or a pharmaceutically acceptable salt thereof and Pridopidine or a pharmaceutically acceptable salt thereof for the treatment of a subject afflicted with a movement disorder, wherein the Tetrabenazine or a pharmaceutically acceptable salt thereof and the Pridopidine or a pharmaceutically acceptable salt thereof are administered simultaneously, separately or sequentially.

In an embodiment, the movement disorder is Huntington's disease, Tourette's syndrome, or tardive dyskinesia.

The subject invention also provides a product containing an amount of Tetrabenazine or a pharmaceutically acceptable salt thereof and an amount of Pridopidine or a pharmaceutically acceptable salt thereof for simultaneous, separate or sequential use in treating a subject afflicted with a movement disorder.

In an embodiment, the movement disorder is Huntington's disease, Tourette's syndrome, or tardive dyskinesia.

The subject invention also provides a method of treating a subject afflicted with obesity, an obesity associated disorder or a cardiovascular side effect of Pridopidine comprising administering to the subject a combination of a therapeutically effective amount of Pridopidine or a pharmaceutically acceptable salt thereof, and a therapeutically effective amount of Tetrabenazine or a pharmaceutically acceptable salt thereof, wherein the amounts when taken together are effective to treat the subject.

In an embodiment, the subject is a human patient.

The subject invention also provides a combination of Pridopidine, or a pharmaceutically acceptable salt thereof; and Tetrabenazine, or a pharmaceutically acceptable salt thereof; for the treatment, prevention or alleviation of obesity, or an obesity associated disorder, and for treatment, prevention or alleviation of the cardiovascular side effects of Pridopidine, in a mammal, including a human.

In another aspect, the present invention relates to a combination therapy in which a pharmaceutically effective amount of Pridopidine, or a pharmaceutically acceptable salt thereof, is administered together with a therapeutically effective amount of Tetrabenazine, or a pharmaceutically acceptable salt thereof, for the treatment, prevention or alleviation of a movement disorder.

In a preferred embodiment the hyperkinetic movement disorder is an involuntary hyperkinetic movement disorder arising from Huntington's disease, Gilles de la Tourette's syndrome, or tardive dyskinesia, and in particular an involuntary hyperkinetic movement disorder arising from Huntington's disease.

Viewed from another aspect, the invention provides a combination of Pridopidine, or a pharmaceutically acceptable salt thereof, and Tetrabenazine, or a pharmaceutically acceptable salt thereof, for use as a medicament.

In another aspect, the invention relates to the use of a combination of
(i) Pridopidine, or a pharmaceutically acceptable salt thereof; and
(ii) Tetrabenazine, or a pharmaceutically acceptable salt thereof;
for the manufacture of a medicament for the treatment, prevention or alleviation of a movement disorder of a mammal, including a human.

In another aspect, the invention provides pharmaceutical compositions comprising Pridopidine, or a pharmaceutically acceptable salt thereof, for use in a combination therapy together with Tetrabenazine, or a pharmaceutically acceptable salt thereof, for the treatment, prevention or alleviation of a hyperkinetic movement disorder.

In another aspect the invention provides a method for the treatment, prevention or alleviation of a hyperkinetic movement disorder in a living animal body, which method comprises the step of administering to such animal bodies in need thereof, a therapeutically effective amount of Pridopidine, or a pharmaceutically acceptable salt thereof; in a combination therapy with Tetrabenazine, or a pharmaceutically acceptable salt thereof.

In another aspect the invention provides a pharmaceutical composition comprising a therapeutically effective amount of Pridopidine, or a pharmaceutically acceptable salt thereof, and a therapeutically effective amount of Tetrabenazine, or a pharmaceutically acceptable salt thereof.

In a further aspect the invention provides for a kit of parts comprising at least two separate unit dosage forms (A) and (B), wherein (A) comprises Pridopidine, or a pharmaceutically acceptable salt thereof; and (B) comprises Tetrabenazine, or a pharmaceutically acceptable salt thereof, and optionally (C), instructions for the simultaneous, sequential or separate administration of the Pridopidine of (A) and the Tetrabenazine of (B), to a patient in need thereof.

In a further aspect the invention provides an article of manufacture, comprising (A) a first pharmaceutical dosage form comprising Pridopidine, or a pharmaceutically acceptable salt thereof; and (B) a second pharmaceutical dosage form comprising Tetrabenazine, or a pharmaceutically acceptable salt thereof; wherein the article contains first and second pharmaceutical dosage forms.

In a further aspect the invention provides a method of treating a subject afflicted with a movement disorder comprising administering to the subject a combination of a therapeutically effective amount of Pridopidine or a pharmaceutically acceptable salt thereof, and a therapeutically effective amount of Tetrabenazine or a pharmaceutically acceptable salt thereof, wherein the amounts when taken together are effective to treat the human patient.

In an embodiment, the movement disorder is an involuntary hyperkinetic movement disorder arising from Huntington's disease, Gilles de la Tourette's syndrome, or tardive dyskinesia.

In an embodiment, the movement disorder is an involuntary hyperkinetic movement disorder arising from Huntington's disease In a further aspect the invention provides a method of treating a mammal, including a human, afflicted with an obesity, or an obesity associated disorder or of the cardiovascular side effects of Pridopidine comprising administering to the subject a combination of a therapeutically effective amount of Pridopidine or a pharmaceutically acceptable salt thereof, and a therapeutically effective amount of Tetrabenazine or a pharmaceutically acceptable salt thereof, wherein the amounts when taken together are effective to treat a mammal.

In an embodiment, the therapeutically effective amount of Pridopidine or the pharmaceutically acceptable salt thereof, and the therapeutically effective amount of Tetrabenazine or the pharmaceutically acceptable salt thereof are administered orally.

In an embodiment, the therapeutically effective amount of Pridopidine or the pharmaceutically acceptable salt thereof, and the therapeutically effective amount of Tetrabenazine or the pharmaceutically acceptable salt thereof are administered intravenously.

In an embodiment, the therapeutically effective amount of Pridopidine or the pharmaceutically acceptable salt thereof, and the therapeutically effective amount of Tetrabenazine or the pharmaceutically acceptable salt thereof are administered by direct penetration of the drug through the stratum corneum.

The Pridopidine containing medicament may be applied simultaneously with Tetrabenazine, in a sequential manner, or by separate administration. Preferably Pridopidine is given at the same time as Tetrabenazine.

It is currently believed that Pridopidine may be used (co-administered with Tetrabenazine) in a therapeutically effective amount in the range of about 0.01-1000 mg API daily, more preferred in the range of about 1-500 mg API daily, even more preferred in the range of about 10-200 mg API daily.

It is currently believed that Tetrabenazine may be used (co-administered with Pridopidine) in a therapeutically effective amount in the range of about 0.01-1000 mg API daily, more preferred in the range of about 1-500 mg API daily, even more preferred in the range of about 10-200 mg API daily.

Pridopidine and Tetrabenazine may be co-administered by any conventional route. In a preferred embodiment Pridopidine and Tetrabenazine are administered either orally, intravenously, intravascularly, intraperitoneally, sub-cutaneously, intramuscularly, inhalatively, topically, by patch, or by suppository.

In a more preferred embodiment Pridopidine and Tetrabenazine are administered orally (p.o.).

In another more preferred embodiment Pridopidine and Tetrabenazine are administered intravenously (i.v.).

In another embodiment Pridopidine and Tetrabenazine are administered by subcutaneous (s.c.) injection.

Any combination of two or more of the embodiments described herein is considered within the scope of the present invention.

Pharmaceutically Acceptable Salts

The active compounds for use according to the invention may be provided in any form suitable for the intended administration. Suitable forms include pharmaceutically (i.e. physiologically) acceptable salts, and pre- or prodrug forms of the compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzene-sulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

Pharmaceutical Compositions

While the compounds for use according to the invention may be administered in the form of the raw compound, it is preferred to introduce the active ingredients, optionally in the form of physiologically acceptable salts, in a pharmaceutical composition together with one or more adjuvants, excipients, carriers, buffers, diluents, and/or other customary pharmaceutical auxiliaries.

In a preferred embodiment, the invention provides pharmaceutical compositions comprising the active compounds or pharmaceutically acceptable salts or derivatives thereof, together with one or more pharmaceutically acceptable carriers therefore, and, optionally, other therapeutic and/or prophylactic ingredients know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition of the invention can be manufactured by the skilled person by use of standard methods and conventional techniques appropriate to the desired formulation. When desired, compositions adapted to give sustained release of the active ingredient may be employed.

Further details on techniques for formulation and administration may be found in the latest edition of *Remington's Pharmaceutical Sciences* (Maack Publishing Co., Easton, Pa.).

The actual dosage of each of the active ingredients depends on the nature and severity of the disease being treated, the exact mode of administration, form of administration and is within the discretion of the physician, and may be varied by titration of the dosage to the particular circumstances of this invention to produce the desired therapeutic effect. However, the below dosages for the compound and the anti-obesity compound are considered suitable.

The dosage of the compound is determined as the API (Active Pharmaceutical Ingredient), i.e. calculated as the free base.

A daily dosage in the range of about 0.1-2 mg API daily, preferably of about 0.25-1 mg API daily, especially 0.25, 0.5 or 1.0 mg API daily, is suitable for therapeutic treatments. The daily dosage of the compound may be administered in one or several doses, such as two, per day. In one embodiment, the daily dosage is administered in one dose.

The daily dosage of the anti-obesity compound is presently contemplated to be in the range of about 0.1-500 mg of active ingredient depending on the actual compound. More specific dosage intervals may be in the range of about 0.1-2 mg, about 1-10 mg, about 10-50 mg, about 25-100 mg, about 50-200 mg and about 100-500 mg daily. The daily dosage of the anti-obesity compound may be administered in one or several doses, such as two, per day. In one embodiment, the daily dosage is administered in one dose.

As used herein, "effective" as in an amount effective to achieve an end means the quantity of a component that is sufficient to yield an indicated therapeutic response without undue adverse side effects (such as toxicity, irritation, or allergic response) commensurate with a reasonable benefit/risk ratio when used in the manner of this disclosure. For example, an amount effective to treat a movement disorder. The specific effective amount will vary with such factors as the particular condition being treated, the physical condition of the patient, the type of mammal being treated, the duration of the treatment, the nature of concurrent therapy (if any), and the specific formulations employed and the structure of the compounds or its derivatives.

As used herein, to "treat" or "treating" encompasses, e.g., inducing inhibition, regression, or stasis of the disorder and/or disease. As used herein, "inhibition" of disease progression or disease complication in a subject means preventing or reducing the disease progression and/or disease complication in the subject.

As used herein, "combination" means an assemblage of reagents for use in therapy either by simultaneous or contemporaneous administration. Simultaneous administration refers to administration of an admixture (whether a true mixture, a suspension, an emulsion or other physical combination) of the Pridopidine and the Tetrabenazine. In this case, the combination may be the admixture or separate containers of the Pridopidine and the Tetrabenazine that are combined just prior to administration. Contemporaneous administration refers to the separate administration of the Pridopidine and the Tetrabenazine at the same time, or at times sufficiently close together that a synergistic activity or an activity that is additive or more than additive relative to the activity of either the Pridopidine or the Tetrabenazine alone is observed.

As used herein, "DOPAC" is 3,4-Dihydroxyphenylacetic acid.

As used herein, "LMA" is Locomotor activity.

As used herein, "TBZ" is Tetrabenazine.

Pharmaceutical Kits of Parts

According to the invention there is also provided a kit of parts comprising at least two separate unit dosage forms (A) and (B), wherein (A) comprises Pridopidine, or a pharmaceutically acceptable salt thereof; and (B) comprises Tetrabenazine, or a pharmaceutically acceptable salt thereof; and optionally (C) instructions for the simultaneous, sequential or separate administration of the Pridopidine of (A) and the Tetrabenazine of (B), to a patient in need thereof.

Pridopidine for use according to the invention and Tetrabenazine for use according to the invention may preferably be provided in a form that is suitable for administration in conjunction with the other. This is intended to include instances where one or the other of two formulations may be administered (optionally repeatedly) prior to, after, and/or at the same time as administration with the other component.

Also, Pridopidine for use according to the invention and Tetrabenazine for use according to the invention may be administered in a combined form, or separately or separately and sequentially, wherein the sequential administration is close in time or remote in time. This may in particular include that two formulations are administered (optionally repeatedly) sufficiently closely in time for there to be a beneficial effect for the patient, that is greater over the course of the treatment of the relevant condition than if either of the two formulations are administered (optionally repeatedly) alone, in the absence of the other formulation, over the same course of treatment. Determination of whether a combination provides a greater beneficial effect in respect of, and over the course of treatment of, a particular condition, will depend upon the condition to be treated or prevented, but may be achieved routinely by the person skilled in the art.

When used in this context, the terms "administered simultaneously" and "administered at the same time as" include that individual doses of Pridopidine and Tetrabenazine are administered within 48 hours, e.g. 24 hours, of each other.

Bringing the two components into association with each other, includes that components (A) and (B) may be provided as separate formulations (i.e. independently of one another), which are subsequently brought together for use in conjunction with each other in combination therapy; or packaged and presented together as separate components of a "combination pack" for use in conjunction with each other in combination therapy.

According to the invention there is also provided an article of manufacture, comprising (A) a first pharmaceutical dosage form comprising Pridopidine, or a pharmaceutically acceptable salt thereof; and (B) a second pharmaceutical dosage form comprising Tetrabenazine, or a pharmaceutically acceptable salt thereof; wherein the article contains first and second pharmaceutical dosage forms.

Methods of Therapy

In another aspect the invention provides methods of treatment, prevention or alleviation of a hyperkinetic movement disorder in a living animal body, including a human, which method comprises the step of administering to such a living animal body in need thereof, a therapeutically effective amount of Pridopidine, or a pharmaceutically acceptable salt thereof; in a combination therapy with Tetrabenazine, or a pharmaceutically acceptable salt thereof.

The hyperkinetic movement disorder may in particular be an involuntary movement disorder arising from Huntington's disease, Gilles de la Tourette's syndrome, or tardive dyskinesia.

In a preferred embodiment, the hyperkinetic movement disorder is an involuntary movement disorder arising from Huntington's disease.

Introduction to the Examples

Motor function is controlled by a complex circuitry connecting the cerebral cortex with subcortical structures including the basal ganglia and the thalamus. One major pathway within this circuitry is the so called "indirect pathway" forming a closed feed-back loop connecting the cortex, the striatum, and the thalamus via a population of striatal GABA-ergic, medium spiny neurons expressing dopamine D2 type receptors. This pathway functions as a negative regulator of movements, and is important for the suppression of excessive movements. Dopamine modulates the indirect pathway by inhibitory dopamine D2 receptors in such a way that increased dopamine tone at these receptors leads to a reduced activity of the indirect pathway, and therefore a reduced ability to suppress movements. On the other hand, a diminished dopamine tone leads to increased activity of the indirect pathway associated with stronger suppression of movements.

Another important cortico-striato-thalamic pathway involved in motor control is the so called "direct pathway", forming a closed, positive feed-back loop via striatal GABA-ergic, medium spiny neurons expressing dopamine D1 type receptors. The direct pathway is a positive modulator of motor function, involved in the selection and enabling of voluntary movements. Dopamine, acting at D1 type receptors, stimulates the striatal GABA-ergic neurons in the direct pathway, thereby enhancing movements. Conversely, a reduction in dopamine tone at these D1 receptors leads to a reduced ability to perform voluntary movements.

The general reduction in dopamine transmission resulting from treatment with Tetrabenazine also reduces other dopamine dependent functions. In particular, the dopamine tone at the direct pathway, with striatal neurons expressing dopamine D1 receptors, is also reduced, leading to a weakening of the direct pathway and therefore to a reduced capacity to perform voluntary movements. Furthermore, the dopamine depletion induced by Tetrabenazine is likely to impair dopamine dependent motivation and reward, which is hypothesised to underlie the pro-depressant adverse effects of Tetrabenazine.

Given that Pridopidine is a pure antagonist at dopamine D2 receptors, with no agonist activity, it was expected that a therapeutic combination of Pridopidine and Tetrabenazine would lead to further reduced tone at dopamine D2 receptors, and therefore to a further reduction in overall locomotor activity, compared to treatment with Tetrabenazine only.

Examples

The invention is further illustrated with reference to the following examples, which are not intended to be in any way limiting to the scope of the invention as claimed.

The examples below explore the interaction between Pridopidine and Tetrabenazine with respect to locomotor activity. Striatal levels of dopamine and DOPAC were also determined. Tetrabenazine reduces tissue levels of dopamine as a direct consequence of the inhibition of VMAT. Both compounds increase striatal DOPAC levels in a dose-dependent manner in vivo, reflecting decreased tone at the dopamine D2 receptor (Ponten 2010; Reches, 1983). Furthermore, the effect on expression of the immediate-early gene Arc (activity-regulated cytoskeleton-associated protein/activity-regulated gene 3.1) was measured in the frontal cortex and striatum. Arc gene expression is a biomarker reflecting synaptic activity (Steward, 2001; Kawashima 2009). Interaction experiments with Tetrabenazine and the dopamine D2 antagonist haloperidol were also performed in order to compare the effects of Pridopidine with those of a classical dopamine D2 receptor antagonist 1) Effect of Tetrabenazine on Locomotor Activity, Striatal DOPAC, and Arc Tetrabenazine was given sc at 0.37, 0.64 and 1.1 mg/kg. LMA was recorded for 60 minutes after dosing. Thereafter rats were sacrificed and brains were collected. Analyses of brain tissues included DOPAC in the striatum, and Arc mRNA in the frontal cortex and striatum.

Tetrabenazine reduced locomotor activity. (FIG. 1). Tetrabenazine dose dependently inhibited spontaneous locomotor activity. When the full hour of recording was considered, the 1.1 mg/kg Tetrabenazine dose group displayed a significant reduction to 40% of the vehicle control group mean ($P<0.01$). During the initial 15 min significant reductions ($P<0.05$) were seen both for the 1.1 and 0.37 mg/kg Tetrabenazine dose groups, whereas for the period 15-60 minutes post dosing significant effects ($P<0.05$) were observed at 0.64 and 1.1 mg/kg. The reduction in locomotor activity reflects the decreased dopamine transmission caused by inhibition of VMAT2.

Figure 2:
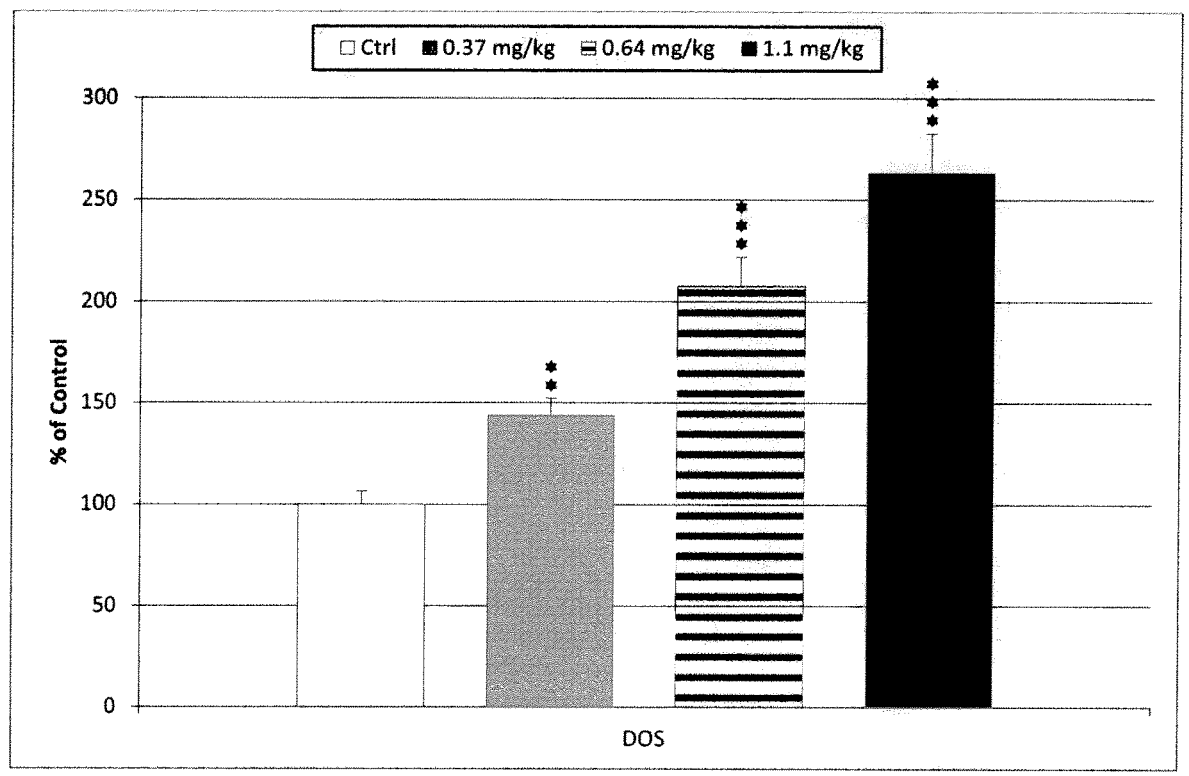
FIG. 2. The effect of Tetrabenazine on striatal DOPAC (3,4-Dihydroxyphenylacetic acid). Animals were allocated into four different treatment groups, n=5. The treatment groups consisted of Vehicle (Glucose 5.5% v/w) and Tetrabenazine tested at three doses (0.37; 0.64 and 1.1 μmol/kg). All compounds were injected s.c. four minutes before start of locomotor activity recording at a volume of 5 ml/kg.

Tetrabenazine dose dependently increases striatal DOPAC, with statistically significant effects at all doses tested. The increase in DOPAC is a neuronal marker of reduced tone at dopamine D2 receptors, due to the decreased dopamine transmission in rats treated with Tetrabenazine. See Table 1 and FIG. 1-2.

Arc in striatum and cortex: Tetrabenazine increased striatal Arc and reduced frontal cortex Arc. Tetrabenazine dose dependently increased Arc mRNA in the striatum, reaching 147% of the vehicle control group mean ($P<0.01$) at the highest dose tested (1.1 mg/kg). In the frontal cortex, a significant reduction of Arc mRNA down to 66% of the vehicle control group mean was observed at Tetrabenazine dose of 1.1 mg/kg ($P<0.05$). At Tetrabenazine dose of 0.64 mg/kg, there was a trend towards a reduction in frontal cortex mRNA (83% of control group mean, $p=0.14$). See FIG. 3. The Arc increase in the striatum is most likely due to reduced tone at dopamine D2 receptors. The Arc decrease in the frontal cortex is likely to be related to decreased dopamine transmission in the cortex leading to a reduced tone at dopamine D1 receptors.

2) Effect of Pridopidine on Locomotor Activity, Striatal DOPAC, and Arc

Figure 4:
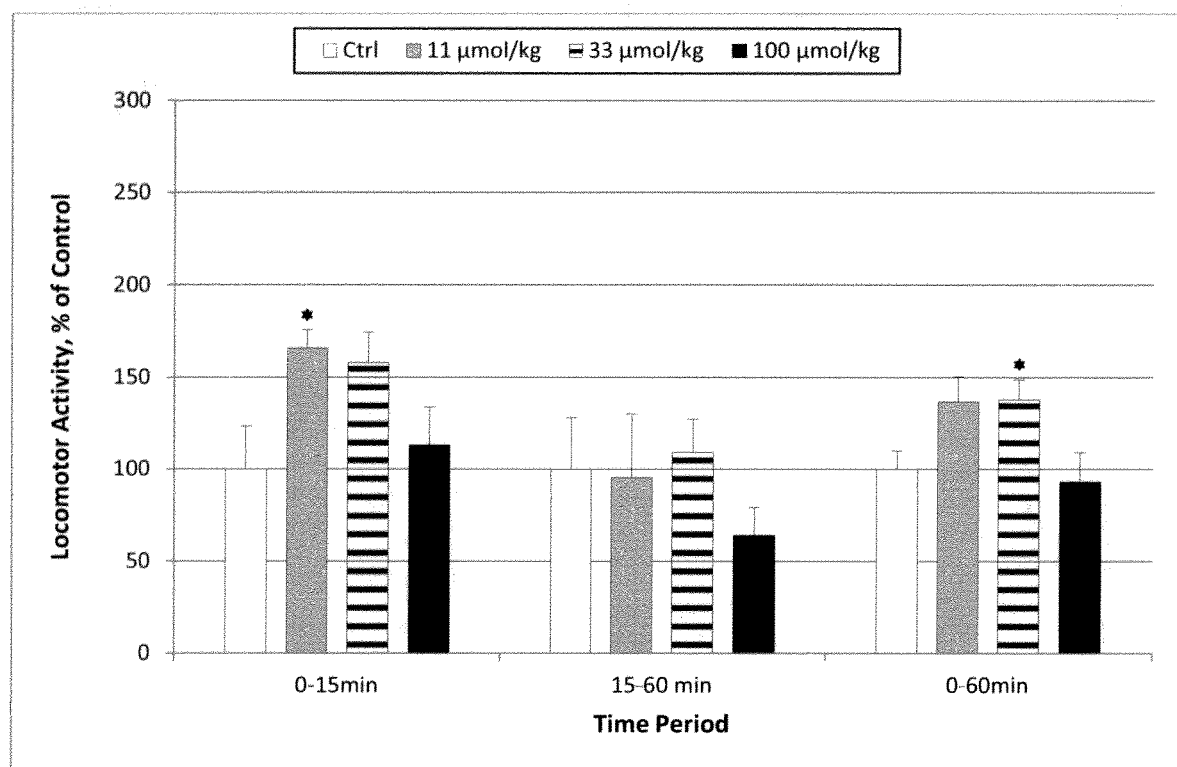
FIG. 4. Spontaneous locomotor activity expressed as a percentage of the mean control group value for Pridopidine. Activity is shown by dose for each recorded time period. Animals were allocated into four different treatment groups, n=5. The treatment groups consisted of Vehicle (saline; NaCl 0.9% v/w) and Pridopidine tested at three doses (11; 33 and 100 μmol/kg). All compounds were injected s.c. four minutes before start of locomotor activity recording at a volume of 5 ml/kg.

Pridopidine was given sc at 11, 33 and 100 µmol/kg. Pridopidine displayed no inhibitory effect on spontaneous locomotor activity. A slight increase in locomotor activity was observed at the mid dose, 33 µmol/kg, over the full 60 minute recording period. See FIG. 4. When the full hour of recording was examined, a significant increase in locomotor activity to 138% of the vehicle control group mean was observed for the 33 µmol/kg Pridopidine dose group ($P<0.05$). During the initial 15 min a significant increase ($P<0.05$) was seen for the 11 µmol/kg Pridopidine dose group, whereas for the period 15-60 minutes post dosing no significant effects were observed.

Figure 5:
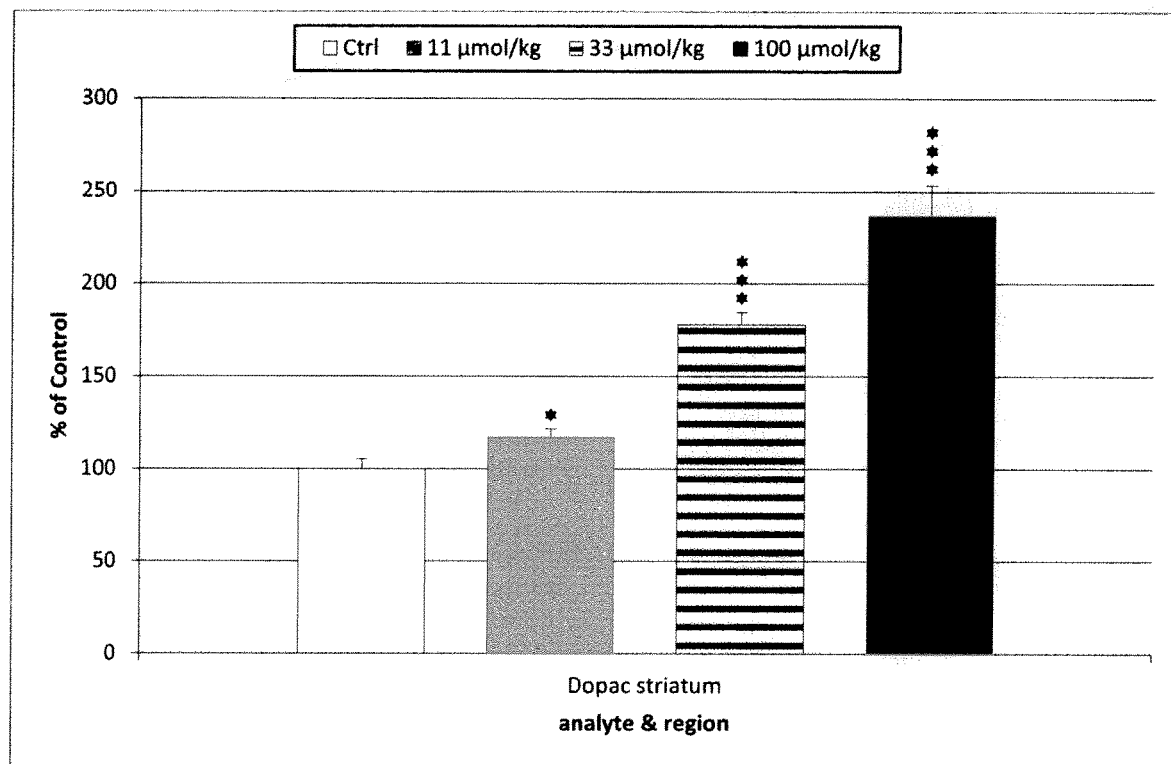
FIG. 5. The effect of Pridopidine (NS30016) on striatal DOPAC. Animals were allocated into four different treatment groups, n=5. The treatment groups consisted of Vehicle (saline; NaCl 0.9% v/w) and Pridopidine tested at three doses (11; 33 and 100 μmol/kg). All compounds were injected s.c. four minutes before start of locomotor activity recording at a volume of 5 ml/kg.

Pridopidine dose dependently increases striatal DOPAC, with statistically significant effects at all doses tested. The increase in DOPAC is a neuronal marker of reduced tone at dopamine D2 receptors, due to dopamine D2 receptor antagonism exerted by Pridopidine. See FIG. 5 and Table 1.

Figure 6:
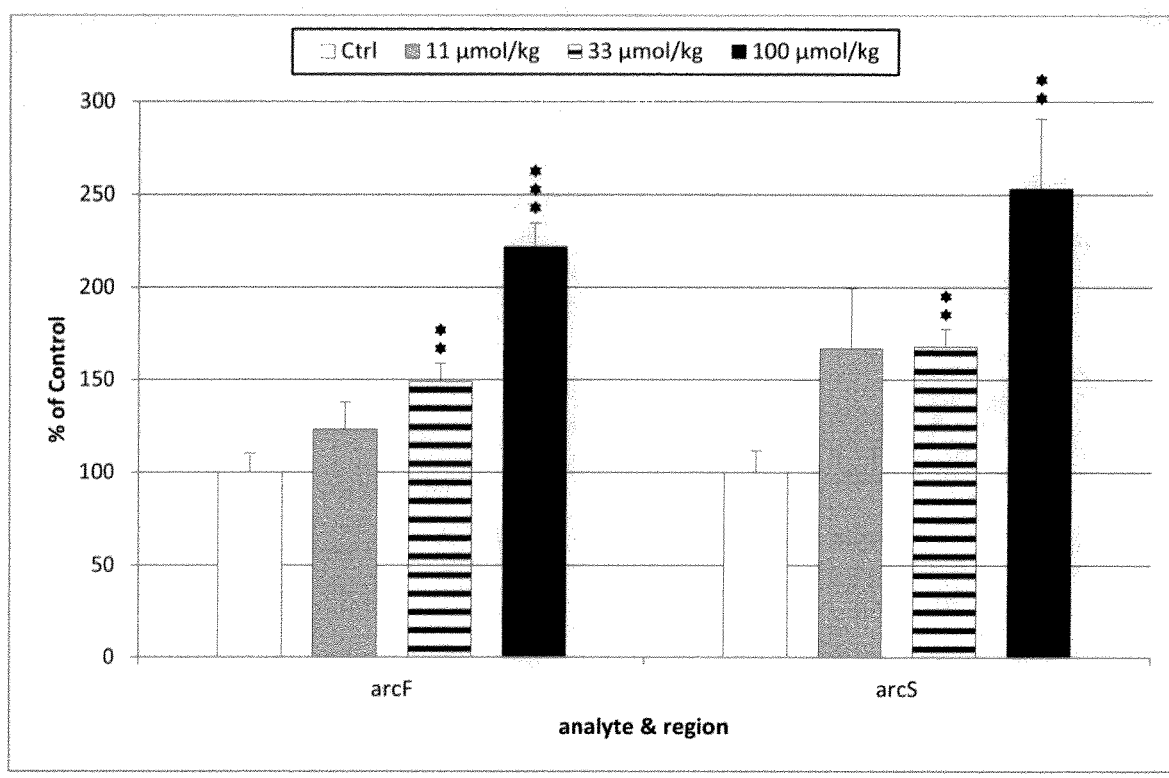
FIG. 6. Arc gene expression expressed as a percentage of the mean control group value, following treatment with Pridopidine. Expression is shown by dose and by region (striatal arc (arcS) or frontal cortex arc (arcF)). Animals were allocated into four different treatment groups, n=5. The treatment groups consisted of Vehicle (saline; NaCl 0.9% v/w) and Pridopidine tested at three doses (11; 33 and 100 μmol/kg). All compounds were injected s.c. four minutes before start of locomotor activity recording at a volume of 5 ml/kg.

Pridopidine dose-dependently increased striatal and cortical arc gene expression, reaching statistical significance at the highest doses tested. Pridopidine increased Arc mRNA levels in the frontal cortex in a dose-dependent manner, up to 149% ($p<0.01$) and 222% ($p<0.001$) of the vehicle control group mean at doses of 33 µmol/kg and 100 µmol/kg, respectively (FIG. 6). Pridopidine increased Arc mRNA levels in the striatum in a dose-dependent manner. Compared with the relevant control group means, levels reached 168% and 253% ($p<0.01$ for both doses at Pridopidine 33 µmol/kg and 100 µmol/kg, respectively). (FIG. 6). The Arc increase in the striatum is most likely due to reduced tone at dopamine D2 receptors. The Arc increase in the frontal cortex is likely to be related to increased dopamine transmission in the cortex leading to an increased tone at dopamine D1 receptors.

3) Effect of Haloperidol on Locomotor Activity, Striatal DOPAC, and Arc

Figure 7:
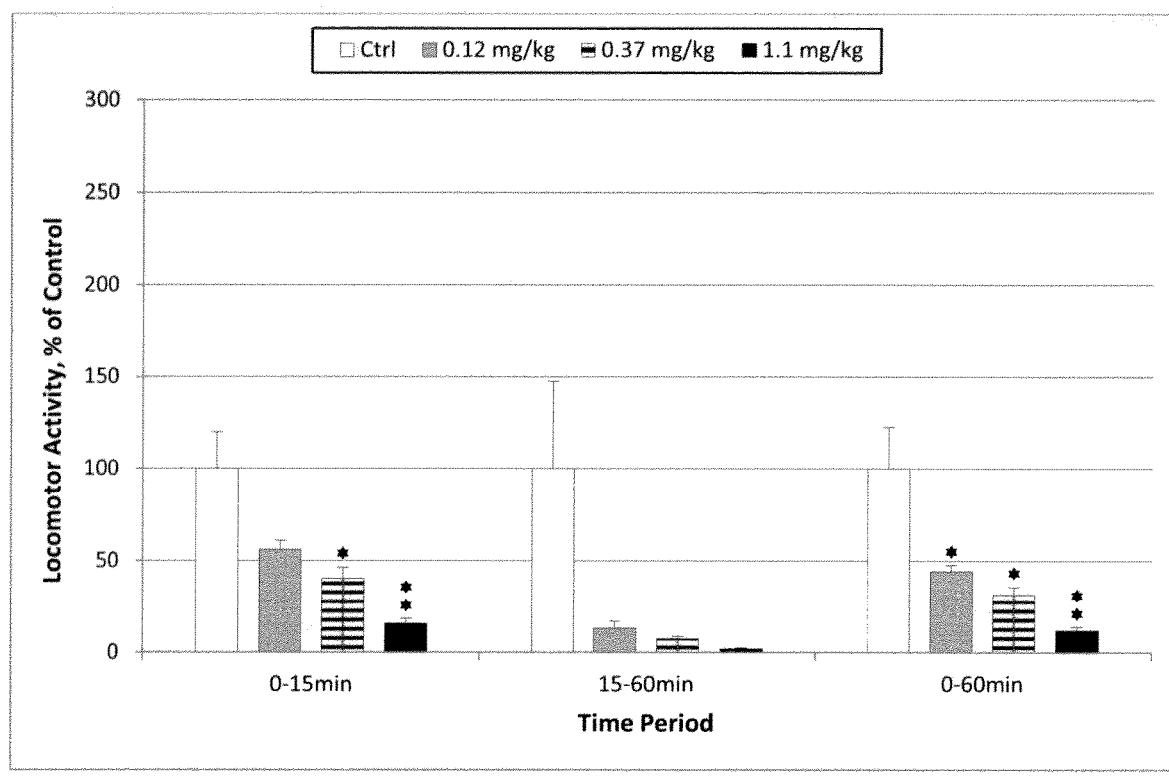
FIG. 7. Spontaneous locomotor activity expressed as a percentage of the mean control group value for haloperidol. Activity is shown by dose for each recorded time period. Animals were allocated into four different treatment groups, n=5. The treatment groups consisted of Vehicle (Glucose 5.5% v/w) and Haloperidol tested at three doses (0.12; 0.37 and 1.1 μmol/kg). All compounds were injected s.c. four minutes before start of locomotor activity recording at a volume of 5 ml/kg.
Figure 8:
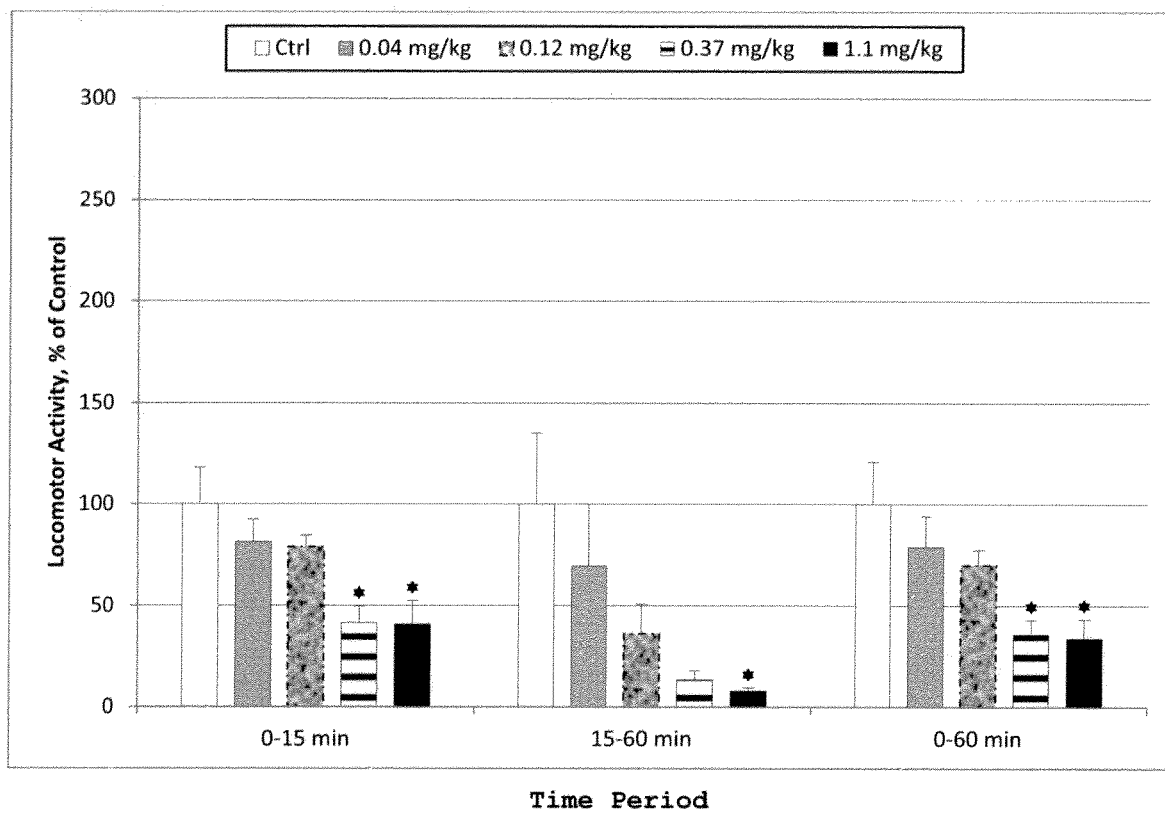
FIG. 8. Spontaneous locomotor activity expressed as a percentage of the mean control group value for haloperidol. Animals were allocated into five different treatment groups, n=4. The treatment groups consisted of Vehicle (Glucose 5.5% v/w) and Haloperidol tested at four doses (0.04; 0.12; 0.37 and 1.1 μmol/kg). All compounds were injected s.c. four minutes before start of locomotor activity recording at a volume of 5 ml/kg.

Haloperidol was given sc at 0.12, 0.37 and 1.1 mg/kg (See FIG. 7). In an additional experiment assessing effects at lower doses, 0.04, 0.12. 0.37 and 1.1 mg was given (See FIG. 302). Haloperidol displayed a dose-dependent inhibitory effect on spontaneous locomotor activity. Statistically significant effects were observed at 0.12 mg/kg and higher doses, but not at the lowest dose tested, 0.04 mg/kg.

More specifically, when the full hour of recording was considered, the 0.37 and 1.1 mg/kg haloperidol dose groups displayed significant reductions to about 35% of the vehicle control group mean ($P<0.05$). During the initial 15 min, significant reductions ($P<0.05$) were seen both for the 0.37 and 1.1 mg/kg haloperidol dose groups, whereas for the period 15-60 minutes post dosing a significant effect ($P<0.05$) was observed for the 1.1 mg/kg dose group only.

Figure 9:
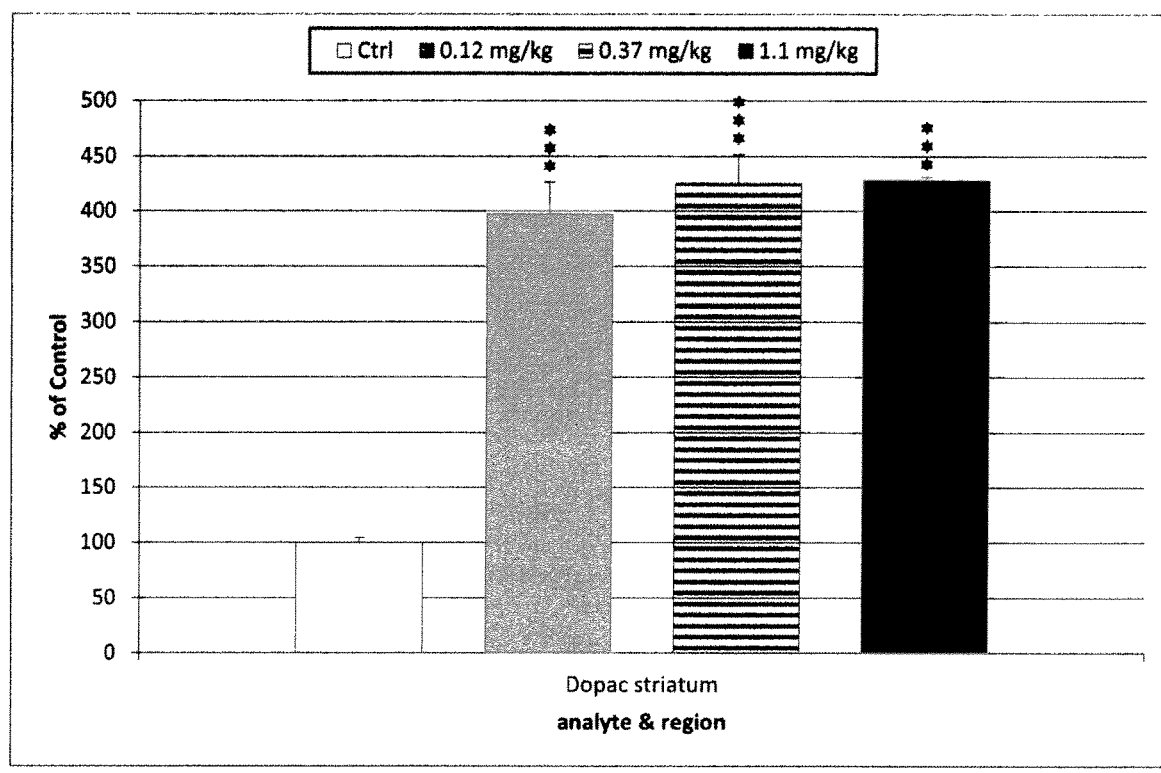
FIG. 9. The effect of Haloperidol on striatal DOPAC. Animals were allocated into four different treatment groups, n=5. The treatment groups consisted of Vehicle (Glucose 5.5% v/w) and Haloperidol tested at three doses (0.12; 0.37 and 1.1 μmol/kg). All compounds were injected s.c. four minutes before start of locomotor activity recording at a volume of 5 ml/kg.

Haloperidol dose dependently increases striatal DOPAC, with statistically significant effects at all doses tested. The increase in DOPAC is a neuronal marker of reduced tone at dopamine D2 receptors, due to dopamine D2 receptor antagonism. See Table 1 and FIG. 9.

Figure 11:
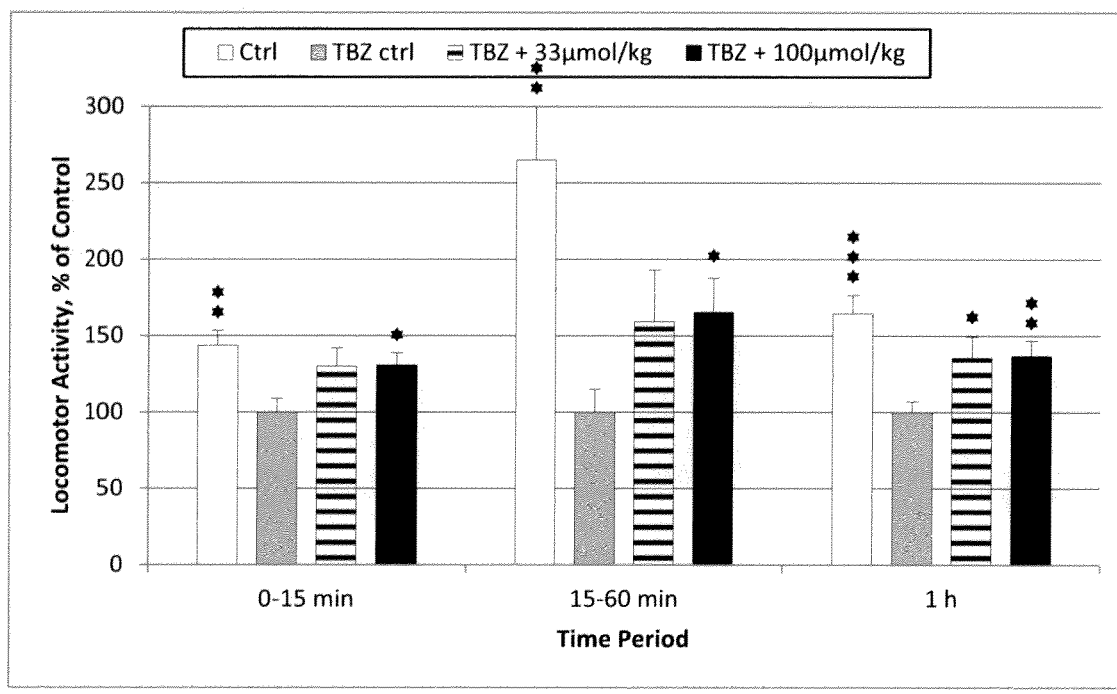
FIG. 11. Spontaneous locomotor activity expressed as a percentage of the mean control group value for Tetrabenazine+Pridopidine. Activity is shown by dose for each recorded time period. This experiment was completed in one of two ways: (1) "Process BS81" in which the animals were allocated into four different treatment groups, n=5, the treatment groups consisted of Vehicle 1:1 (saline; NaCl 0.9% v/w+5.5% glukos with a few drops of HAc) the second group consisted of a single dose of Tetrabenazine (0.64 mg/kg) and the third and fourth groups consisted of Pridopidine tested in two doses (33 and 100 μmol/kg together with Tetrabenazine in one dose (0.64 mg/kg) or (2) "Process TA284" in which the animals were allocated into four different treatment groups, n=10, the treatment groups consisted of Vehicle 1:1 (saline; NaCl 0.9% v/w+5.5% glukos with a few drops of HAc) the second group consisted of a single dose of Tetrabenazine (0.64 mg/kg) and the third and fourth groups consisted of Pridopidine tested in two doses (33 and 100 μmol/kg together with Tetrabenazine in one dose (0.64 mg/kg). No brain tissue was collected from this experiment. All compounds were injected s.c. four minutes before start of locomotor activity recording at a volume of 5 ml/kg.

Haloperidol dose dependently increased Arc mRNA in the striatum, reaching 262% (P<0.01), 331% (P<0.001), 409% (P<0.01), respectively, of the vehicle control group mean at the 0.12 mg/kg, 0.37 mg/kg and 1.1 mg/kg doses. The Arc increase in the striatum is most likely due to reduced tone at dopamine D2 receptors. There was no significant effect of Haloperidol on cortical Arc gene expression. See FIG. 10.

treated controls for the full hour of recording (P<0.001), as well for both the 0-15 min period (P<0.01) and the 15-60 min period (P<0.01). Considering the full hour of recording, Pridopidine reversed the locomotor inhibition induced by Tetrabenazine at both the 33 and the 100 μmol/kg dose groups, reaching 135% (P<0.05) and 137% (P<0.01), respectively of Tetrabenazine control mean. During the 0-15 min as well as for the 15-60 min periods this reversing effect reached significance for the Pridopidine 100 μmol/kg dose group. This implies that the tone at striatal D2 receptors is further reduced when adding Pridopidine to monoamine depleted animals. See FIG. 11.

TABLE 1

Effects on striatal DOPAC in drug-naive and Tetrabenazine-treated rats

| Test compound | Dose group | Dose-response in naive rats DOPAC striatum | Dose-response in naive rats DA striatum | Interaction with Tetrabenazine DOPAC striatum | Interaction with Tetrabenazine DA striatum |
|---|---|---|---|---|---|
| Tetrabenazine |  | 100 ± 6 | 100 ± 6 | — | — |
|  | 0.37 mg/kg | 144 ± 8** | 48 ± 2*** | — | — |
|  | 0.64 mg/kg | 208 ± 14*** | 33 ± 3*** | — | — |
|  | 1.1 mg/kg | 263 ± 19*** | 20 ± 2*** | — | — |
| Pridopidine | C | 100 ± 5 | 100 ± 3 | 53 ± 1†† | 299 ± 13††† |
|  | TC | — | — | 100 ± 11 | 100 ± 10 |
|  | 11 μmol/kg | 117 ± 5* | 104 ± 3 | — | — |
|  | 33 μmol/kg | 178 ± 7*** | 101 ± 3 | 123 ± 8 | 91 ± 11 |
|  | 100 μmol/kg | 236 ± 17*** | 73 ± 4** | 155 ± 4†† | 98 ± 8 |
| Haloperidol | C | 100 ± 22 | 100 ± 5 | 65 ± 3††† | 202 ± 9††† |
|  | TC | — | — | 100 ± 3 | 100 ± 8 |
|  | 0.04 mg/kg | 171 ± 35 | 95 ± 5 | 187 ± 6††† | 79 ± 3† |
|  | 0.12 mg/kg | 276 ± 8*** | 78 ± 3** | 218 ± 12††† | 87 ± 10 |
|  | 0.37 mg/kg | 254 ± 17** | 79 ± 5* | — | — |
|  | 1.1 mg/kg | 292 ± 10*** | 81 ± 2* | — | — |

Data are shown as mean ± SEM DOPAC levels, expressed as percentages of control group mean.
C, vehicle control group;
DOPAC, 3,4-dihydroxyphenylacetic acid;
TC, Tetra-benazine control group
*p < 0.05;
p < 0.01*;
p < 0.001 vs. vehicle control group;
†p < 0.05;
††p < 0.01;
†††p < 0.001 vs. Tetrabenazine control group.

In summary, while all three antidopaminergic compounds produced increased striatal DOPAC, and increased striatal arc gene expression, both effects most likely related to decreased tone at dopamine D2 receptors, Pridopidine was unique in that it did not inhibit locomotor activity. Another feature differentiating Pridopidine from Haloperidol or Tetrabenazine, is that it increased cortical Arc gene expression.

Combination Experiments

To test the effect of dopamine D2 antagonist when administered to partially dopamine depleted animals, Haloperidol and Pridopidine were combined with Tetrabenazine at a dose that produced submaximal but significant effects on striatal dopac and locomotor activity.

4) Effect of Pridopidine on Tetrabenazine Induced Locomotor Activity Reduction, Striatal Dopamine Increase, and Arc In the interaction experiment with Pridopidine and Tetrabenazine, Pridopidine was given at 33 and 100 μmol/kg, combined with Tetrabenazine at 0.64 mg/kg. See FIG. 11. The locomotor recordings demonstrated that Pridopidine reversed the behavioural inhibition induced by Tetrabenazine. However, the effects on striatal DOPAC were additive, i.e. coadministration of Pridopidine further increased striatal DOPAC.

Figure 12:
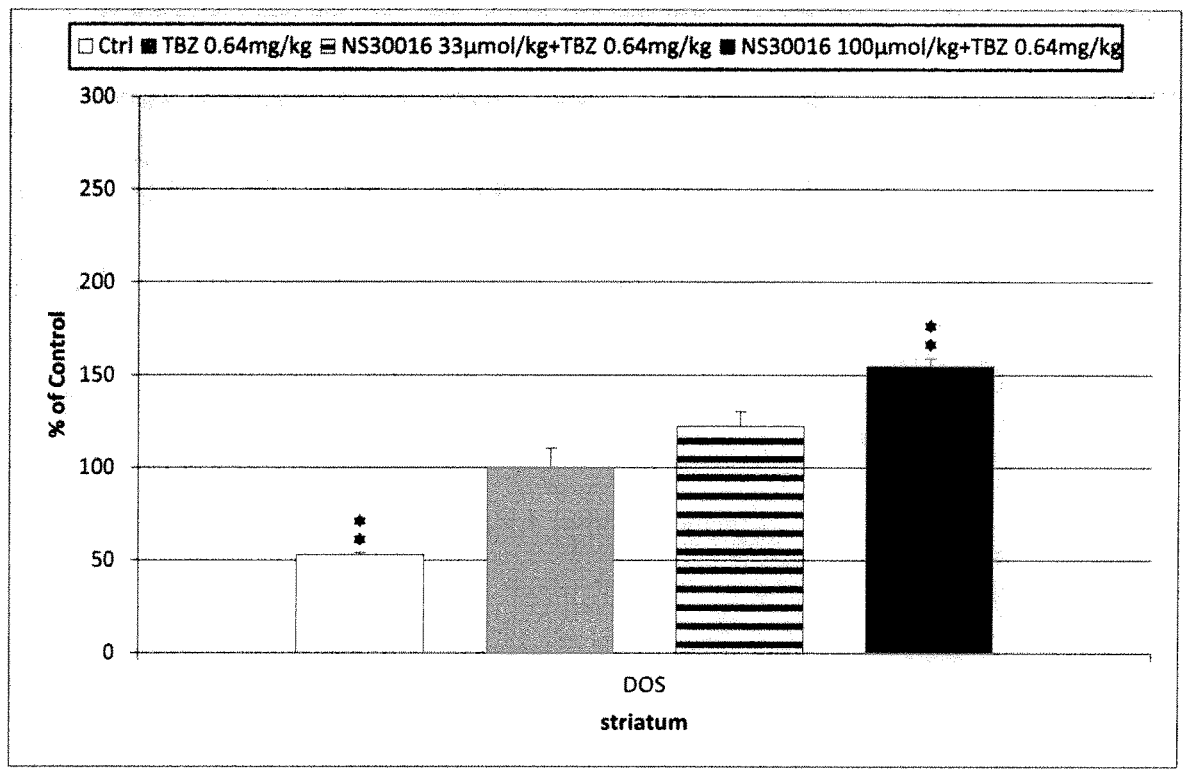
FIG. 12. The effect of Pridopidine on Tetrabenazine induced striatal dopamine increase. Animals were allocated into four different treatment groups, n=5. The treatment groups consisted of Vehicle 1:1 (saline; NaCl 0.9% v/w+5.5% glukos with a few drops of HAc) the second group consisted of a single dose of Tetrabenazine (0.64 mg/kg) and the third and fourth groups consisted of Pridopidine (NS30016) tested in two doses (33 and 100 μmol/kg together with Tetrabenazine in one dose (0.64 mg/kg). All compounds were injected s.c. four minutes before start of locomotor activity recording at a volume of 5 ml/kg.

For the locomotor inhibition, there was a significant decrease in the Tetrabenazine control group vs. vehicle In the interaction experiment where Tetrabenazine 0.64 mg/kg was combined with either Pridopidine 33 μmol/kg or 100 μmol/kg, Tetrabenazine induced a significant increase in striatal DOPAC levels was seen compared with the vehicle-treated control group (p<0.01; Table 1). Pridopidine further increased DOPAC levels in striatum, reaching 155% of the Tetrabenazine control group mean at the 100 μmol/kg dose (p<0.01). See Table 1 and FIG. 12.

Likewise, striatal Arc expression was further increased by adding Pridopidine. In contrast, the Arc decrease induced by Tetrabenazine was counteracted by Pridopidine.

Figure 13:
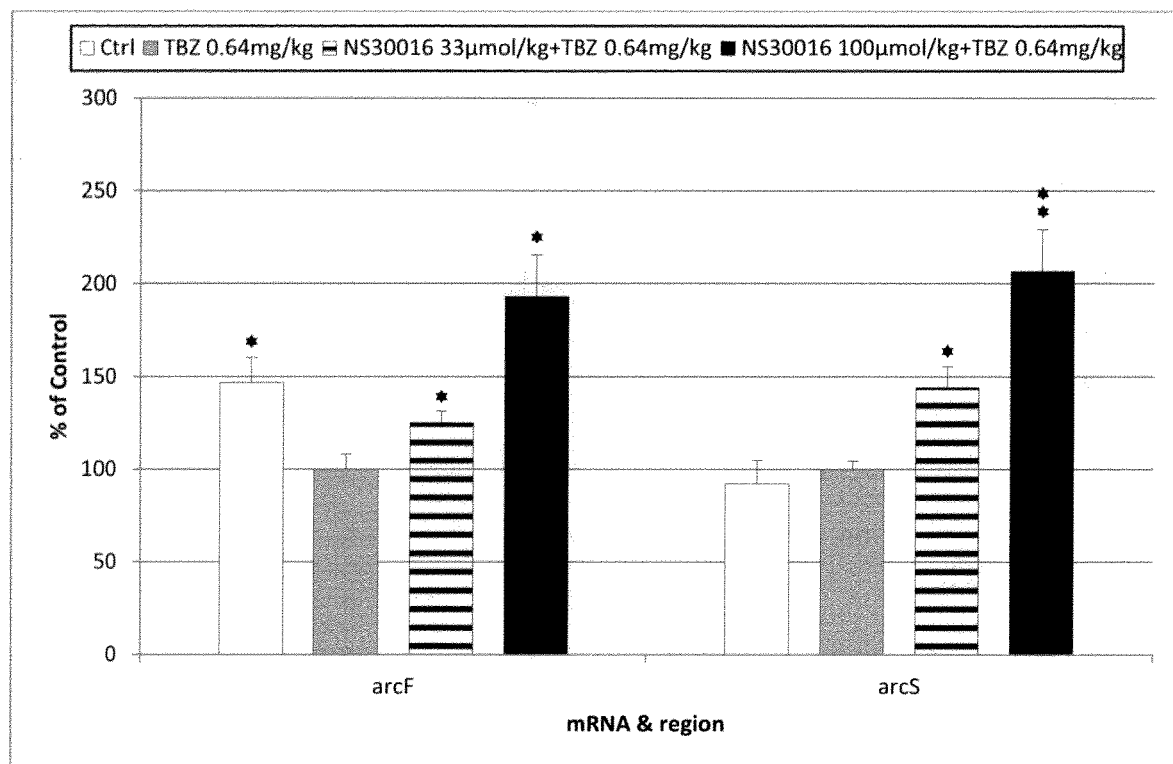
FIG. 13. Arc gene expression expressed as a percentage of the mean control group value, following treatment with Tetrabenazine+Pridopidine. Expression is shown by dose and by region (striatal arc (arcS) or frontal cortex arc (arcF)). Animals were allocated into four different treatment groups, n=5. The treatment groups consisted of Vehicle 1:1 (saline; NaCl 0.9% v/w+5.5% glukos with a few drops of HAc) the second group consisted of a single dose of Tetrabenazine (0.64 mg/kg) and the third and fourth groups consisted of Pridopidine tested in two doses (33 and 100 μmol/kg together with Tetrabenazine in one dose (0.64 mg/kg All compounds were injected s.c. four minutes before start of locomotor activity recording at a volume of 5 ml/kg.

Pridopidine reversed the decrease in frontal cortex Arc induced by Tetrabenazine as shown in FIG. 13. More specifically, Tetrabenazine had no significant effect on striatal Arc mRNA at the 0.64 mg/kg dose used in the interaction experiment. Pridopidine, when coadministered with Tetrabenazine, dose dependently increased striatal Arc, reaching 144% (P<0.05) and 207% (P<0.01), respectively, of the Tetrabenazine control group mean at the 33 μmol/kg, and the 100 μmol/kg doses of Pridopidine.

Figure 3:
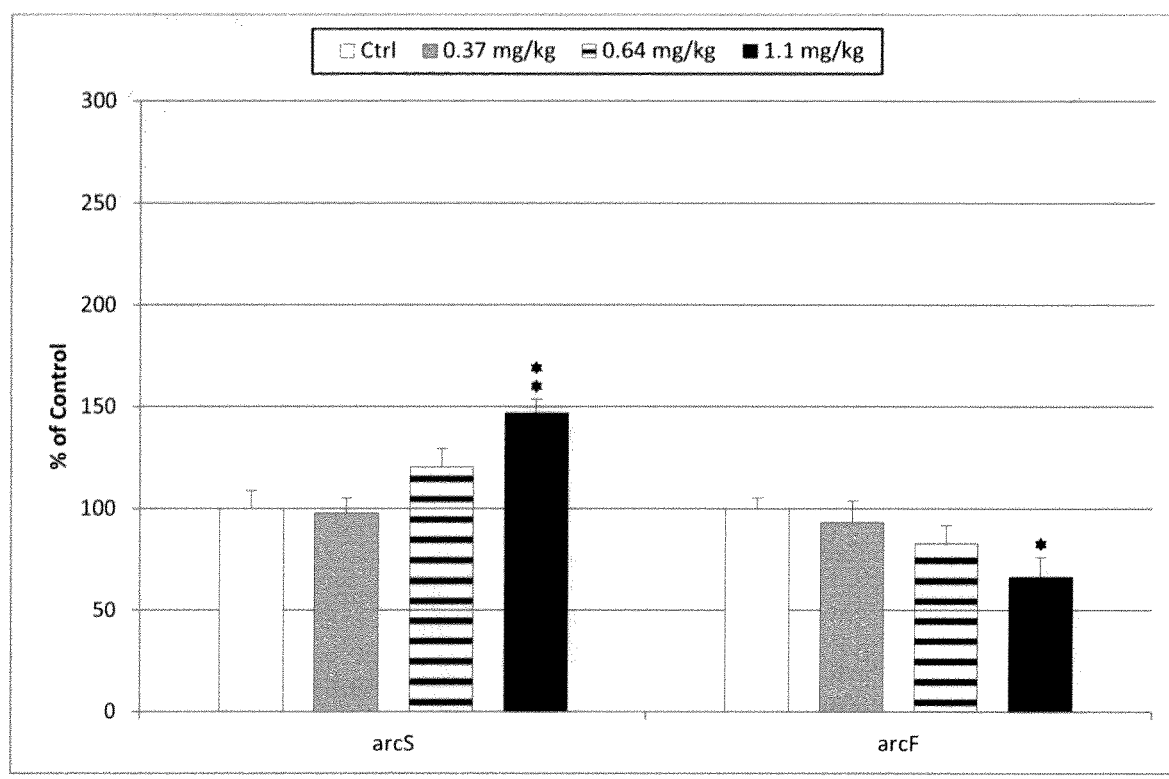
FIG. 3. Arc gene expression (Arc mRNA levels or Arc) expressed as a percentage of the mean control group value, following treatment with Tetrabenazine. Expression is shown by dose and by region (striatal arc (arcS) or frontal cortex arc (arcF)). Animals were allocated into four different treatment groups, n=5. The treatment groups consisted of Vehicle (Glucose 5.5% v/w) and Tetrabenazine tested at three doses (0.37; 0.64 and 1.1 μmol/kg). All compounds were injected s.c. four minutes before start of locomotor activity recording at a volume of 5 ml/kg.

Tetrabenazine induced a significant decrease (P<0.05) in frontal cortex Arc mRNA, which is in accordance with the trend towards a decrease of frontal cortex Arc mRNA at the 0.64 mg/kg dose observed in the dose response experiment with Tetrabenazine (FIG. 3). Pridopidine dose dependently reversed the decrease in frontal cortex Arc mRNA induced by Tetrabenazine. At 33 µmol/kg and 100 µmol/kg of Pridopidine, Arc mRNA was increased to 125% (P<0.05) and 193% (P<0.05), respectively, of the Tetrabenazine control group mean 5) Effect of Haloperidol on Tetrabenazine Induced Locomotor Activity Reduction, Striatal Dopamine Increase, and Arc In the interaction experiment with Haloperidol and Tetrabenazine, Haloperidol was given at 0.04 and 0.12 mg/kg, combined with Tetrabenazine at 0.64 mg/kg.

Figure 14:
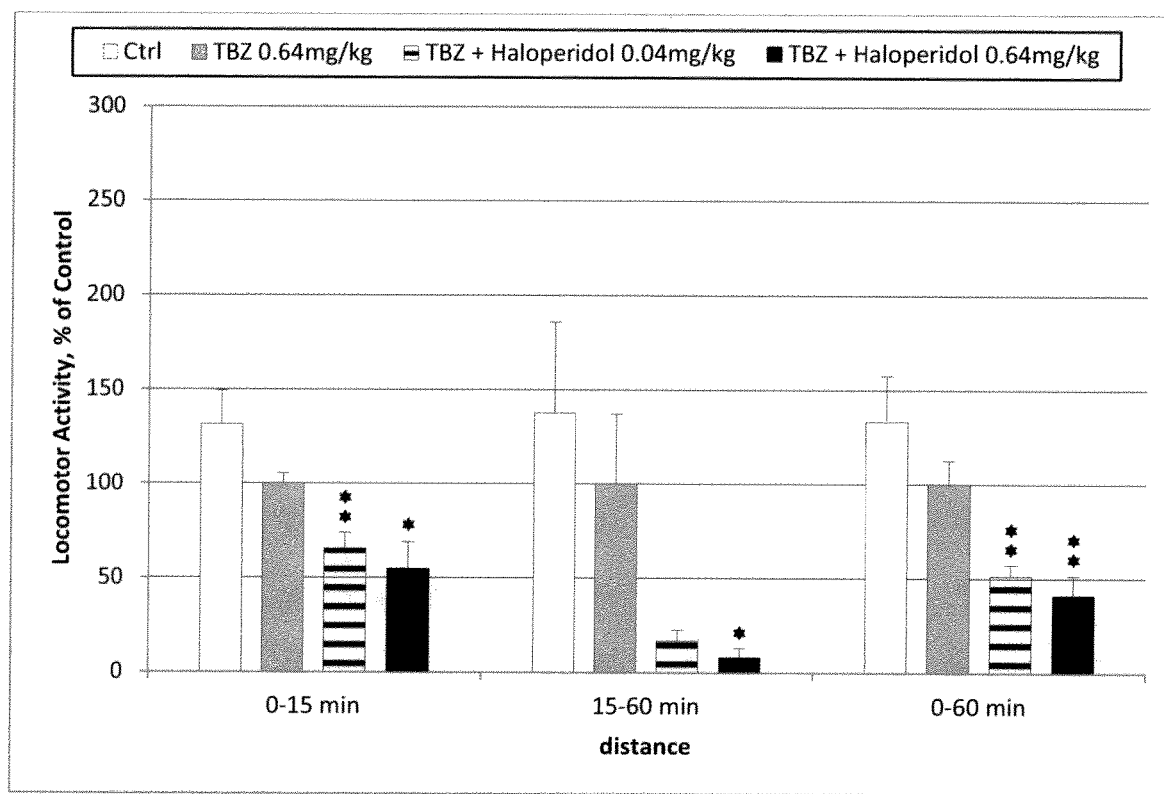
FIG. 14. Spontaneous locomotor activity expressed as a percentage of the mean control group value for Tetrabenazine+haloperidol. Activity is shown by dose for each recorded time period. Animals were allocated into four different treatment groups, n=5. The treatment groups consisted of Vehicle 1:1 (saline; NaCl 0.9% v/w+5.5% glukos with a few drops of HAc) the second group consisted of a single dose of Tetrabenazine (0.64 mg/kg) and the third and fourth groups consisted of Haloperidol tested in two doses (0.04 and 0.12 mg/kg together with Tetrabenazine in one dose (0.64 mg/kg). All compounds were injected s.c. four minutes before start of locomotor activity recording at a volume of 5 ml/kg.

The locomotor recordings showed that Haloperidol further reduced locomotor activity in animals treated with Tetrabenazine. More specifically, the locomotor recording over the full hour demonstrated that haloperidol significantly (P<0.01) reduced locomotor activity in rats treated with Tetrabenazine both at the 0.04 and 0.12 mg/kg doses, down to 51% and 41% of Tetrabenazine control group mean, respectively. For the first 15 min of recording this reducing effect was significant at both the 0.04 mg/kg (P<0.01) and the 0.12 mg/kg (P<0.05) doses, whereas for the 15-60 min period the reduction was significant for the 0.12 mg/kg dose only (P<0.05). See FIG. 14.

Figure 15:
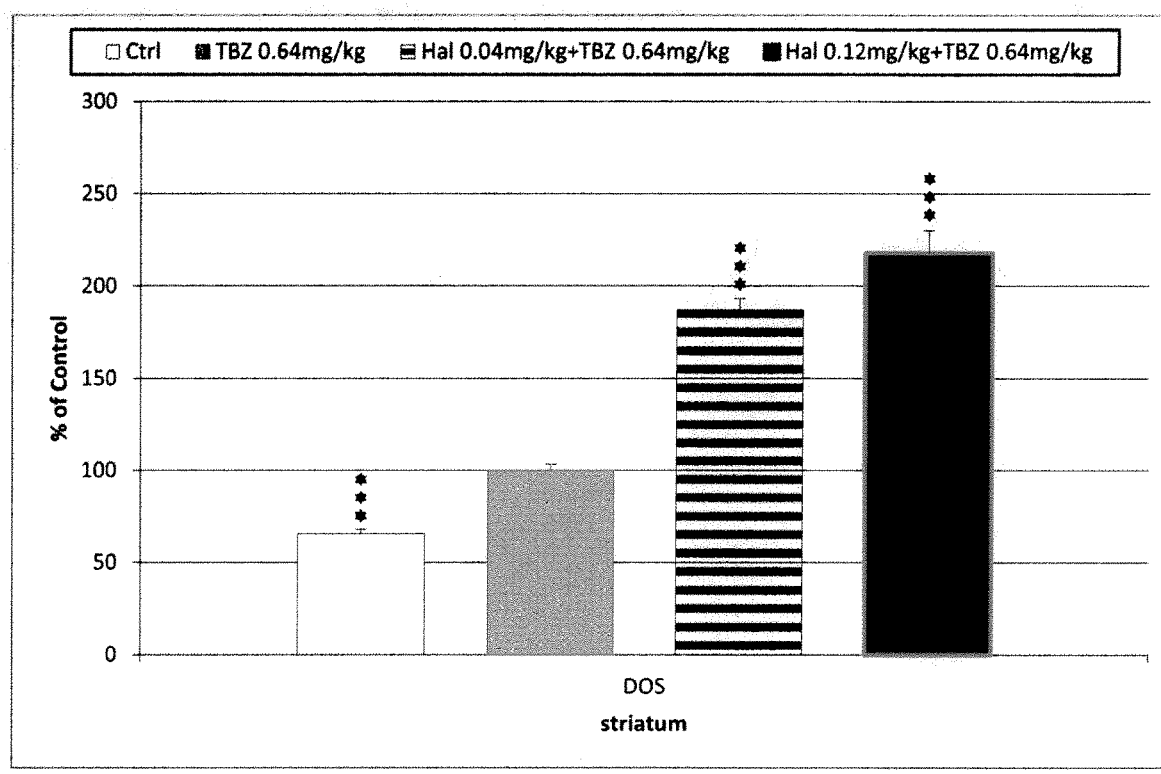
FIG. 15. The effect of Haloperidol on Tetrabenazine induced striatal dopamine increase. Animals were allocated into four different treatment groups, n=5. The treatment groups consisted of Vehicle 1:1 (saline; NaCl 0.9% v/w+5.5% glukos with a few drops of HAc) the second group consisted of a single dose of Tetrabenazine (0.64 mg/kg) and the third and fourth groups consisted of Haloperidol tested in two doses (0.04 and 0.12 mg/kg together with Tetrabenazine in one dose (0.64 mg/kg). All compounds were injected s.c. four minutes before start of locomotor activity recording at a volume of 5 ml/kg.

The effects on striatal DOPAC were additive, i.e. coadministration of Haloperidol with Tetrabenazine caused additional increases in striatal DOPAC. In the interaction experiment where Tetrabenazine 0.64 mg/kg was combined with haloperidol 0.04 mg/kg or 0.12 mg/kg, Tetrabenazine induced a significant increase in striatal DOPAC levels compared with the vehicle-treated control group (p<0.001; Table 1). Haloperidol further increased DOPAC levels in striatum, reaching 187% and 218% of the Tetrabenazine control group mean at the 0.04 mg/kg and 0.12 mg/kg doses, respectively (p<0.001 for both doses). See Table 1 and FIG. 15.

Figure 16:
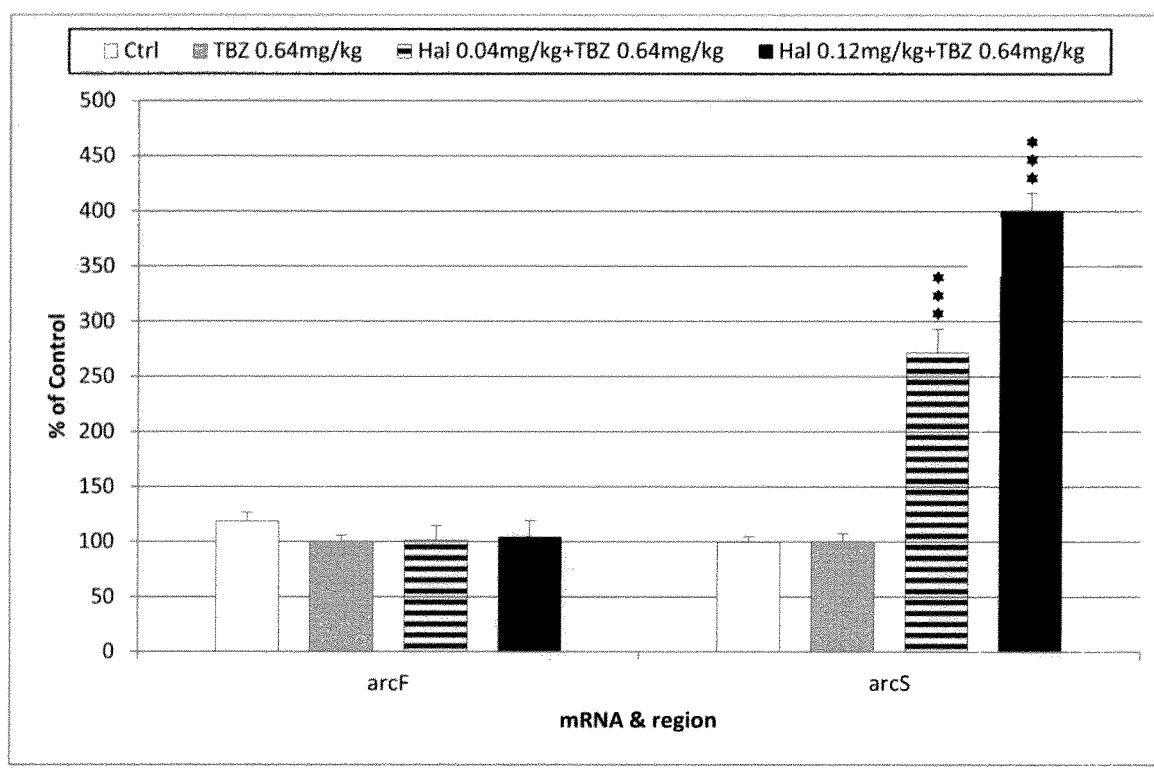
FIG. 16. Arc gene expression expressed as a percentage of the mean control group value, following treatment with Tetrabenazine+haloperidol. Expression is shown by dose and by region (striatal arc (arcS) or frontal cortex arc (arcF)). Animals were allocated into four different treatment groups, n=5. The treatment groups consisted of Vehicle 1:1 (saline; NaCl 0.9% v/w+5.5% glukos with a few drops of HAc) the second group consisted of a single dose of Tetrabenazine (0.64 mg/kg) and the third and fourth groups consisted of Haloperidol tested in two doses (0.04 and 0.12 mg/kg together with Tetrabenazine in one dose (0.64 mg/kg). All compounds were injected s.c. four minutes before start of locomotor activity recording at a volume of 5 ml/kg.

There was no significant effect of Haloperidol on cortical Arc gene expression in rats co-treated with Tetrabenazine. Haloperidol further increases striatal Arc in Tetrabenazine treated animals (FIG. 16). Tetrabenazine had no significant effect on striatal Arc mRNA at the 0.64 mg/kg dose used in the interaction experiment. Haloperidol, when coadministered with Tetrabenazine, dose dependently increased striatal Arc, reaching 272% (P<0.001) and 400% (P<0.001), respectively, of the Tetrabenazine control group mean at the 0.04 mg/kg, and the 0.12 mg/kg doses of haloperidol.

Tetrabenazine tended to decrease frontal cortex Arc mRNA (P=0.08), which is in accordance with the trend towards a decrease of frontal cortex Arc mRNA at the 0.64 mg/kg dose observed in the dose response experiment with Tetrabenazine (FIG. 3), and the significant decrease observed in the interaction experiment with Pridopidine and Tetrabenazine (FIG. 13). There was no significant effect of haloperidol on frontal cortex Arc mRNA in Tetrabenazine treated animals.

Test Methods

The following tests are used for evaluation of the compounds for use according to the invention.

Animals

Male Sprague-Dawley rats from B&K Scanbur (Sollentuna, Sweden) (IBBS58), Charles River (Koln, Germany) (KR104, BS31) or Taconic (Ejby, Denmark) (BS85, BS81, KR219, TA284) were used. Rats weighed 160-180 g at the time of arrival. Rats weighed 220-260 g at the time of the locomotor and tissue neurochemistry studies. Animals were housed five animals per cage with lights on between 06:00 and 18:00. All experiments were carried out in accordance with Swedish animal protection legislation and with the approval of the local Animal Ethics Committee in Gothenburg.

Dosing

IBBS58: Animals were allocated into four different treatment groups, n=5. The treatment groups consisted of Vehicle (saline; NaCl 0.9% v/w) and ACR16 tested at three doses (11; 33 and 100 µmol/kg).

BS31: Animals were allocated into four different treatment groups, n=5. The treatment groups consisted of Vehicle (Glucose 5.5% v/w) and Haloperidol tested at three doses (0.12; 0.37 and 1.1 µmol/kg).

KR104: Animals were allocated into five different treatment groups, n=4. The treatment groups consisted of Vehicle (Glucose 5.5% v/w) and Haloperidol tested at four doses (0.04; 0.12; 0.37 and 1.1 µmol/kg).

KR219: Animals were allocated into four different treatment groups, n=5. The treatment groups consisted of Vehicle (Glucose 5.5% v/w) and Tetrabenazine tested at three doses (0.37; 0.64 and 1.1 µmol/kg).

BS81: Animals were allocated into four different treatment groups, n=5. The treatment groups consisted of Vehicle 1:1 (saline; NaCl 0.9% v/w+5.5% glukos with a few drops of HAc) the second group consisted of a single dose of Tetrabenazine (0.64 mg/kg) and the third and fourth groups consisted of NS30016 tested in two doses (33 and 100 µmol/kg together with Tetrabenazine in one dose (0.64 mg/kg).

TA284: Animals were allocated into four different treatment groups, n=10. The treatment groups consisted of Vehicle 1:1 (saline; NaCl 0.9% v/w+5.5% glukos with a few drops of HAc) the second group consisted of a single dose of Tetrabenazine (0.64 mg/kg) and the third and fourth groups consisted of NS30016 tested in two doses (33 and 100 µmol/kg together with Tetrabenazine in one dose (0.64 mg/kg). No brain tissue was collected from this experiment.

BS85: Animals were allocated into four different treatment groups, n=5. The treatment groups consisted of Vehicle 1:1 (saline; NaCl 0.9% v/w+5.5% glukos with a few drops of HAc) the second group consisted of a single dose of Tetrabenazine (0.64 mg/kg) and the third and fourth groups consisted of Haloperidol tested in two doses (0.04 and 0.12 mg/kg together with Tetrabenazine in one dose (0.64 mg/kg).

All compounds were injected s.c. four minutes before start of locomotor activity recording at a volume of 5 ml/kg.

In Vivo Test: Behaviour

Behavioural activity is measured using eight Digiscan activity monitors (RXYZM (16) TAO, Omnitech Electronics, Columbus, Ohio, USA), connected to an Omnitech Digiscan analyzer and an Apple Macintosh computer equipped with a digital interface board (NB DIO-24, National Instruments, USA). Each activity monitor consists of a quadratic metal frame equipped with photobeam sensors. During measurements of behavioural activity, a rat is put in a transparent acrylic cage with matted black floor (W×L×H, 41×41×30 cm) which in turn is placed in the activity monitor. Each activity monitor is equipped with three rows of infrared photobeam sensors, each row consisting of 16 sensors. Two rows are placed along the front and the side of the floor of the cage, at a 90 degree angle, and the third row is placed 10 cm above the floor to measure vertical activity. Photobeam sensors are spaced 2.5 cm apart. Each activity monitor is fitted in an identical sound and light attenuating box (W×L×H—55×55×45) containing a weak house light and a fan.

The computer software is written using object oriented programming (LabVIEW™, National instruments, Austin, Tex., USA).

Behavioural data from each activity monitor, representing the position (horizontal center of gravity and vertical activity) of the animal at each time, are recorded at a sampling frequency of 25 Hz and collected using a custom written LABView™ application. The data from each recording session are stored and analyzed with respect to distance travelled. Each behavioural recording session lasts 60 min, starting approximately 4 min after the injection of test compound. The results are presented as counts/60 minutes, counts/45 minutes or counts/15 minutes, in arbitrary length units. Statistical comparisons are carried out using Student's t-test against the control group.

In Vivo Test: Neurochemistry

Immediately after the behavioural activity sessions, the rats are decapitated and their brains rapidly taken out and put on an ice-cold petri-dish.

Brains were dissected into striatum, limbic region (containing the nucleus accumbens—both core and shell, amygdala, most parts of the olfactory tubercle and ventral pallidum), frontal cortex and hippocampus. Tissue samples were immediately frozen and stored at −80° C. until it was homogenized with perchloric acid (PCA) (0.1M), ethylenediamine-tetraacetic acid (EDTA) (5.37 mM), glutathione (GSH) (0.65 mM) and alpha-methyl-dopamine (0.25 µM) as internal standard. A digital sonifier (Branson Digital Sonifier 250-D) was used to homogenise tissue from the striatum and limbic region. Cortex tissue was homogenised using an Ultra Turrax T25 homogeniser. All samples were centrifuged at 10.000 rpm for 10 minutes at +4° C. Cortex tissue was filtered in Munktell filter paper 5.5 cm quality 1 F. Tissue eluates were analysed with respect to tissue concentrations (ng/g tissue) of the monoamine transmitter substances (Norepinephrine (NA), dopamine (DA), 5-hydroxytryptamine (5-HT)) as well as their amine metabolites (normetanephrine (NM), 3-methoxytyramine (3-MT)) and acid metabolites (3,4-dihydroxyphenylalanine (DOPAC), 5-hydrocyindoleacetic acid (5-HTAA), homovanillic acid (HVA)) by HPLC separations and electrochemical detection (HPLC/EC). Stock standards (DA, NA, 5-HT, 3-MT, DOPAC, HVA, HIAA, 500 µg/ml) and internal standard (AMDA 500 µg/ml) are prepared once every three months. 5-HT and 5HIAA are dissolved in milliQ water. DA, NA, DOPAC, NM, 3-MT and HVA are dissolved in 0.01 M HCl. 5-HT, 5-HIAA, NM and HVA are kept in fridge; DA, DOPAC, NA and 3-MT are kept in freezer. Standard solution for analyses containing standards diluted in homogenising solution to a concentration of 0.05 µg/ml is prepared daily.

The analytical method is based on two chromatographic separations dedicated for amines or acids. Two chromatographic systems share a common auto injector with a 10-port valve and two sample loops for simultaneous injection on the two systems. Both systems are equipped with a reverse phase column (Luna C18(2), dp 3 µm, 50×2 mm i.d., Phenomenex) and electrochemical detection is accomplished at two potentials on glassy carbon electrodes (MF-1000, Bioanalytical Systems, Inc.). The column effluent is passed via a T-connection to the detection cell or to a waste outlet. This is accomplished by two solenoid valves, which block either the waste or detector outlet. By preventing the chromatographic front from reaching the detector, better detection conditions are achieved. The aqueous mobile phase (0.4 ml/min) for the acid system contains citric acid 14 mM, sodium citrate 10 mM, MeOH 15% (v/v) and EDTA 0.1 mM. Detection potentials relative to Ag/AgCl reference are 0.45 and 0.60V. The aqueous ion pairing mobile phase (0.5 ml/min) for the amine system contains citric acid 5 mM, sodium citrate 10 mM, MeOH 9% (v/v), MeCN 10.5% v/v), decane sulfonic acid 0.45 mM, and EDTA 0.1 mM. Detection potentials relative to Ag/AgCl reference are 0.45 and 0.65V.

PCR

The following methods were used for the data shown in FIG. 3, FIG. 13, and FIG. 16:

Total RNA is prepared by the guanidin isothiocyanate method (Chomczynski, 1987). RNA pellets are solved in MQ water and stored at −80° C. The sample concentration is determined spectrophotometrically by a NanoDrop ND-1000. A quality indicator number and an integrity number of r-RNA are measured with an Experion (Bio-Rad) on random samples.

A two-step reversed transcription is performed by using a SuperScript III kit (Invitrogen). 1 µg of total RNA is reversed transcribed with 5 µl 2×RT Reaction Mix, 1 µl RT Enzyme Mix, volume adjusted to 10 µl with DEPC-treated water. 1 U of *E. coli* RNase H is added. cDNA is diluted 40 times and stored at −20° C.

Three sequences (one gene of interest and two reference genes) are amplified together in a triplex PCR-reaction. For real-time PCR measurements: 5 µl of the cDNA reaction is amplified in a 20 µl reaction mixture containing 10 µl Quanta buffer, 3.5 µl MQ, 0.15 µM of each primer and 0.1 µM of each probe. Real-time PCR is measured on CFX96 (Biorad) using the following settings for all genes: 3 min pre-incubation at 95 degrees C. followed by 40 cycles of denaturation at 95 degrees C. for 15 s, annealing and elongation at 60 degrees C. for 1 minut.

Reference genes are HPRT and cyclophilin.

The primer and probe sequences are as follows for measuring of arc:

```
Activity-regulated gene (Arc) (Accession Number
U19866)
Sense:
5'-GGA GTT CAA GAA GGA GTT TC-3'

Antisense:
5'-CCA CAT ACA GTG TCT GGT A-3'

Probe:
CCG CTT ACG CCA GAG GAA CT

Dye:
5'FAM

Quencher:
3'BHQ1

Product size:
149

Hypoxantine phosphoribosyl transferase (HPRT)
(Accession Number AF001282)

Sense:
5'-AGG GAT TTG AAT CAT GTT TG-3'

Antisense:
5'-CTG CTA GTT CTT TAC TGG C-3'

Probe:
TGT AGA TTC AAC TTG CCG CTG TC

Dye:
5'HEX

Quencher:
3'BHQ1
```

-continued

Product size:
121

Cyclophilin A (Accession Number M19533)
Sense:
5'-CTG GAC CAA ACA CAA ATG-3'

Antisense:
5'-ATG CCT TCT TTC ACC TTC-3'

Probe:
TTG CCA TCC AGC CAC TCA GT

Dye:
5'Texas red

Quencher:
3'BHQ2

Product size:
100

Correct PCR products are confirmed by agarose gel electroforesis (2%) PCR products are purified with PCR purification kit from Qiagen (Valencia, Calif., USA). All genes are sequenced at MWG, Germany. The amounts of gene of interests are normalised with the two reference genes HPRT and cyclophilin A.

For the data shown in FIG. 6, the reverse transcription and PCR were performed as follows:

Reversed transcription is performed by using a Thermo-Script kit (Invitrogen). 1 µg of total RNA is reverse transcribed with 25 µmol oligo (dT), 62.5 ng random hexamers, 7.5 U Thermoscript RT, 10 U RNaseOut, 2 µl 5×cDNA Synthesis buffer, 1 mM dNTP, 0.05 M DTT, adjust volume to 10 µl with DEPC-treated water. Then cDNA is diluted 40 times and stored at −20° C.

For real-time singleplex PCR measurements: 0.7 µl of the cDNA reaction is amplified in a 25 µl reaction mixture containing 1×pcr buffer, 0.2 mM dNTP, 3.7 mM MgCl2, 0.15 mM SYBR green, 0.4 µM of primer and 1 U Taq polymerase. Real-time PCR is measured on Icycler (Biorad) using the following settings for all genes: 60 s pre-incubation at 95° C. followed by 40 cycles of denaturation at 95° C. for 20 s, annealing at 56° C. for 20 s, elongation at 72° C. for 30 s.

Analysis of Arc mRNA: Dose-Response and Interaction Studies for Tetrabenazine, Pridopidine, and Haloperidol Total RNA was prepared by the guanidine isothiocyanate method (Schaefer 1984). RNA pellets were dissolved in ultrapure water and stored at −80° C. RNA concentration was determined spectrophotometrically using a NanoDrop ND-1000 (Thermo Scientific, Waltham, Mass., USA). A quality indicator number and an integrity number of ribosomal RNA were determined for random samples using an Experion electrophoresis system (Bio-Rad Laboratories, Hercules, Calif., USA). Reverse transcription was performed using a SuperScript III kit or a ThermoScript kit (both from Life Technologies Europe BV, Stockholm, Sweden). For Tetrabenazine dose-response and interaction studies, 1 µg RNA was reverse-transcribed with 5 µl 2×RT Reaction Mix and 1 µl RT Enzyme Mix (SuperScript III kit); for studies with Pridopidine and haloperidol, 1 µg RNA was reverse-transcribed using a ThermoScript kit with 25 µmol oligo(dT), 62.5 ng random hexamers, 7.5 U ThermoScript reverse transcriptase, 10 U RNaseOut, 2 µl 5×cDNA Synthesis Buffer, 1 mM dNTPs and 0.05 M dithiothreitol. In all studies, cDNA volume was adjusted to 10 µl with diethylpyrocarbonate-treated water. *Escherichia coli* RNase H (1 U) was added, then cDNA was diluted 40 times and stored at −20° C.

cDNA of Arc and two reference genes, hypoxanthine-guanine phosphoribosyltransferase (HPRT) and cyclophilin A, was amplified by real-time PCR in either a triplex reaction (Tetrabenazine studies) or three singleplex reactions (studies with Pridopidine and haloperidol). For the triplex real-time PCR, 5 µl cDNA was amplified in a 20 µl reaction mixture containing 10 µl Quanta buffer (Quanta BioSciences Inc., Gaithersburg, Md., USA), 3.5 µl ultrapure water, 0.15 µM of each primer and 0.1 µM of each probe (the primer and probe sequences used are detailed in Table 3). Products of the triplex real-time PCR were detected on a CFX96 system (Bio-Rad Laboratories, Hercules, Calif., USA) using the following settings for all genes: 3 minutes pre-incubation at 95° C., followed by 40 cycles of denaturation at 95° C. for 15 seconds, and annealing and elongation at 60° C. for 1 minute. For singleplex real-time PCR measurements, 0.7 µl cDNA was amplified in a 25 µl reaction mixture containing 1×PCR buffer, 0.2 mM dNTPs, 3.7 mM MgCl$_2$, 0.15 mM SYBR Green, 0.4 µM of primer (Table 2) and 1 U Taq polymerase. An Icycler detection system (Bio-Rad Laboratories, Hercules, Calif., USA) was used, with the following settings for all genes: 60 seconds pre-incubation at 95° C., followed by 40 cycles of denaturation at 95° C. for 20 seconds, annealing at 56° C. for 20 seconds, elongation at 72° C. for 30 seconds. Correctly sized PCR products were confirmed by electrophoresis in agarose gel (2%); the products were then purified with a PCR purification kit from Qiagen (Valencia, Calif., USA). All genes were sequenced at MWG Biotech (Ebersberg, Germany). The quantity of Arc mRNA was normalized to those of the two reference genes by a standard curve constructed for every gene using six serial four-fold dilutions of purified PCR products.

Primers:

Hypoxantine phosphoribosyl transferase (HPRT)
(Accession Number AF001282)
Sense:
5'-GGC CAG ACT TGT TGG ATT TG-3'

Antisense:
5'-CCG CTG TCT TTT AGG CTT TG-3'

Cyclophilin A (Accession Number M19533)
Sense:
5'-GTC TCT TTT CGC CGC TTG CT-3'

Antisense:
5'-TCT GCT GTC TTT GGA ACT TTG TCT G-3'

Activity-regulated gene (Arc) (Accession
Number U19866)
Sense:
5'-GTC CCA GAT CCA GAA CCA CA-3'

Antisense:
5'-CCT CCT CAG CGT CCA CAT AC-3'

Initial DNA amounts are quantified by a standard curve constructed for every gene using 6 serial 4-fold dilutions of purified PCR products.

Figure 10:
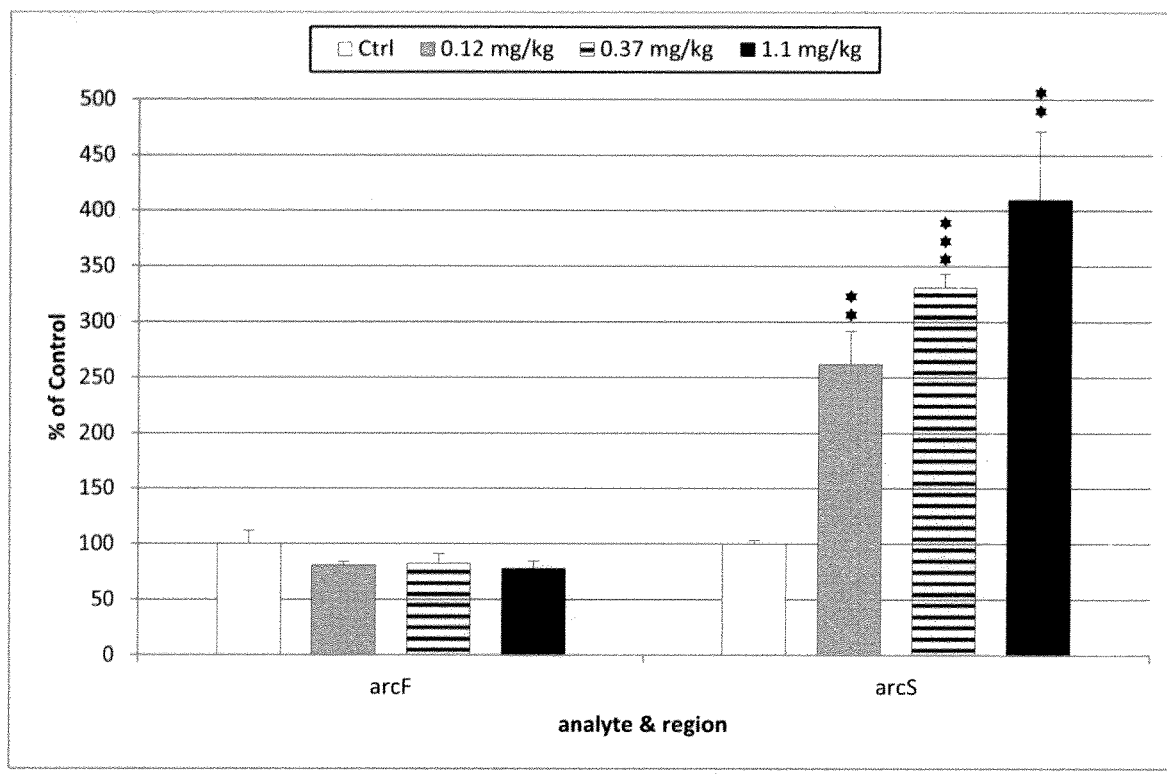
FIG. 10 Arc gene expression expressed as a percentage of the mean control group value, following treatment with haloperidol. Expression is shown by dose and by region (striatal arc (arcS) or frontal cortex arc (arcF)). Animals were allocated into four different treatment groups, n=5. The treatment groups consisted of Vehicle (Glucose 5.5% v/w) and Haloperidol tested at three doses (0.12; 0.37 and 1.1 μmol/kg). All compounds were injected s.c. four minutes before start of locomotor activity recording at a volume of 5 ml/kg.

For the data shown in FIG. 10, the same methods were applied as for the data in FIG. 6, except that the PCR was run on a MyIQ thermal cycler (Biorad).

Discussion of Examples

It was demonstrated that Pridopidine reversed the behavioural inhibition induced by Tetrabenazine. This effect was not shared by haloperidol, which decreased locomotor activity in Tetrabenazine treated animals. The interaction experiments further showed that both Pridopidine and haloperidol retained their characteristic neurochemical effects, ie increases in striatal DOPAC, when co-administered with Tetrabenazine. Likewise, the accompanying increases in striatal arc mRNA levels induced by Pridopidine and haloperidol were maintained in the interaction experiments with Tetrabenazine.

In addition to locomotor depression and increased striatal DOPAC levels, Tetrabenazine produced a dose-dependent decrease in striatal dopamine levels, which was not affected by co-administration of Pridopidine or haloperidol. Moreover, Tetrabenazine produced a dose-dependent increase in frontal cortex Arc mRNA levels. This effect was counteracted in a dose-dependent manner by Pridopidine, but not by haloperidol.

Pridopidine counteracted behavioural depression induced by Tetrabenazine. Consistent with previous data both Tetrabenazine and haloperidol were distinctly inhibitory on spontaneous locomotor activity (Satou 2001, Schaefer 1984), whereas Pridopidine displayed no such effects. This lack of inhibitory effects on spontaneous locomotor activity in rats is part of the characteristic pharmacological profile of Pridopidine (Ponten 2010).

The pharmacological effect of Pridopidine at dopamine D2 receptors was present also when co-administered with Tetrabenazine. The neurochemical analysis demonstrated that all three compounds tested produced a dose dependent increase in striatal DOPAC, reaching around 250-300% of control levels at the top doses applied, in line with previous results. An increase in striatal DOPAC is a common feature of dopamine D2 antagonists, as well as compounds in general producing a reduced tone at central dopamine D2 receptors, including partial agonists with low intrinsic activity, and monoamine depleting drugs (Jordan, 2004; Roffler-Tarlov 1971). The increase seen in striatal DOPAC thus represents a core pharmacological effect of each of the compounds tested. In the interaction experiments, both haloperidol and Pridopidine produced an additional increase in striatal DOPAC, when co-administered with Tetrabenazine. This strongly suggests that the primary effect of Pridopidine and haloperidol was still present in partially monoamine depleted rats. Furthermore, despite the fact that Pridopidine reversed the locomotor-suppressant effect of Tetrabenazine when they were co-administered, the decrease in tissue levels of dopamine induced as a signature effect of Tetrabenazine was unaffected by Pridopidine, suggesting that it did not abolish the pharmacological effects of Tetrabenazine as such.

Overall, the typical neurochemical effects of all three compounds on DOPAC, but also dopamine levels were present throughout the studies indicating that the core effects of each compound on dopaminergic transmission were retained.

The increased Arc mRNA in cortex by Pridopidine co-treatment may help to explain reversal of Tetrabenazine induced locomotor depression. As an additional biomarker of relevance especially for the differentiation of Pridopidine and haloperidol, Arc mRNA was measured in the frontal cortex and the striatum. Arc is an early gene associated with synaptic activation and NMDA receptor signalling, and has previously been reported to increase in the striatum in response to several dopamine D2 antagonists, as well as dopaminergic stabilizers. However there are no previous reports on the effects of Tetrabenazine on Arc gene expression. As demonstrated in the examples, Tetrabenazine induced a significant increase in striatal Arc. Albeit somewhat smaller in magnitude than the effects of Pridopidine and haloperidol, this effect may be related to reduced striatal dopamine transmission also in Tetrabenazine treated animals. As was the case for DOPAC, both Tetrabenazine and Pridopidine produced similar effects on striatal Arc in naive as in Tetrabenazine treated rats.

In the frontal cortex, Tetrabenazine reduced Arc gene expression dose dependently, with significant effects at and above the dose used for the interaction experiments. The dose response studies of Pridopidine and haloperidol, demonstrated a dose dependent increase in frontal cortex Arc gene expression by Pridopidine, but no effects of haloperidol. The ability of Pridopidine to increase frontal cortex Arc gene expression was also evident in Tetrabenazine treated rats. Thus, this pharmacological effect, which distinguishes Pridopidine from haloperidol and other classic dopamine D2 antagonists, was maintained upon partial monoamine depletion. It is conceivable that it represents some degree of cortical synaptic activation that could contribute to the ability of Pridopidine to counteract the behavioural inhibition in Tetrabenazine treated rats. In support of this interpretation, Pridopidine has been shown to increase firing of spontaneously active pyramidal cells in the frontal cortex.

While the examples clearly indicate that the effects of Pridopidine are retained when Pridopidine is co-administered with Tetrabenazine, the combination of Pridopidine and Tetrabenazine did not give rise to any signs of adverse effects. In contrast, combining haloperidol and Tetrabenazine produced pronounced behavioural depression, which would suggest a risk of excessive anti-dopaminergic motor side effects with such a combination in humans, in line with current recommendations on caution regarding co-treatment of patients with Huntington's disease with Tetrabenazine and neuroleptic drugs.

Summary of Dopamine Levels in Striatum

The effects of the different treatments on striatal tissue levels of dopamine are given in Table 1. Tetrabenazine induced a dose dependent reduction in striatal dopamine. At the dose used in the interaction experiments, 0.64 mg/kg, Tetrabenazine reduced striatal dopamine significantly, reaching approximately 50% of vehicle control group mean, throughout the studies performed. Pridopidine and haloperidol both produced smaller decreases in striatal dopamine, at the highest doses tested. In the interaction experiments, the effect of Tetrabenazine on striatal dopamine was essentially unaffected by cotreatment with Pridopidine or haloperidol.

In summary, Pridopidine reversed the behavioural inhibition induced by the monoamine depleting compound Tetrabenazine, while retaining Pridopidine's core neurochemical effects related to dopamine D2 receptor antagonism. Thus, the locomotor depressant effects of Tetrabenazine are alleviated by Pridopidine, despite that the tone at striatal dopamine D2 receptor is further reduced when Pridopidine is administered in addition to Tetrabenazine. Pridopidine also reversed the decrease in frontal cortex Arc gene expression induced by Tetrabenazine. Tentatively, this reflects an activation of cortical neuronal activity that might contribute to the locomotor stimulatory effects of Pridopidine in partially monoamine depleted, hypoactive rats.

TABLE 2

Summary of dose-response and interaction studies

| Study | Prido-pidine | Tetra-benazine | Halo-peridol | Animals per group | Group 1 | Group 2 | Group 3 | Group 4 | Group 5 | Measure(s) |
|---|---|---|---|---|---|---|---|---|---|---|
| 1 | Dose-response study | | | 5[a] | Vehicle[d] | Pridopidine 11 μmol/kg | Pridopidine 33 μmol/kg | Pridopidine 100 μmol/kg | — | Locomotor activity; DOPAC; Arc mRNA |
| 2 | | Dose-response study | | 5[b] | Vehicle[e] | Tetrabenazine 0.37 μmol/kg | Tetrabenazine 0.64 μmol/kg | Tetrabenazine 1.1 μmol/kg | — | Locomotor activity; DOPAC; Arc mRNA |
| 3 | | | Dose-response study | 4[c] | Vehicle[e] | Haloperidol 0.04 mg/kg | Haloperidol 0.12 mg/kg | Haloperidol 0.37 mg/kg | Haloperidol 1.1 mg/kg | Locomotor activity; DOPAC |
| 4 | | | Dose-response study | 5[c] | Vehicle[e] | Haloperidol 0.12 mg/kg | Haloperidol 0.37 mg/kg | Haloperidol 1.1 mg/kg | — | Arc mRNA |
| 5 | Drug interaction study | | | 5[b] | Vehicle[f] | Tetrabenazine 0.64 μmol/kg | Tetrabenazine 0.64 μmol/kg + Pridopidine 33 μmol/kg | Tetrabenazine 0.64 μmol/kg + Pridopidine 100 μmol/kg | — | Locomotor activity; DOPAC; Arc mRNA |
| 6 | Drug interaction study | | | 10[b] | Vehicle[f] | Tetrabenazine 0.64 μmol/kg | Tetrabenazine 0.64 μmol/kg + Pridopidine 33 μmol/kg | Tetrabenazine 0.64 μmol/kg + Pridopidine 100 μmol/kg | — | Locomotor activity |
| 7 | | Drug interaction study | | 5[b] | Vehicle[f] | Tetrabenazine 0.64 μmol/kg | Tetrabenazine 0.64 μmol/kg + haloperidol 0.04 mg/kg | Tetrabenazine 0.64 μmol/kg + haloperidol 0.12 mg/kg | — | Locomotor activity; DOPAC; Arc mRNA |

[a]Animals from Scanbur;
[b]animals from Taconic;
[c]animals from Charles River;
[d]0.9% (w/v) NaCl;
[e]5.5% (w/v) glucose;
[f]1:1 mixture of 0.9% (w/v) NaCl and 5.5% (w/v) glucose adjusted to pH 4.5 with glacial acetic acid

TABLE 3

Primer and probe sequences for measuring expression of Arc and two reference genes

| GenBank accession number | Activity-regulated gene (Arc) U19866 | Hypoxanthine phosphoribosyl transferase (HPRT) AF001282 | Cyclophilin A M19533 |
|---|---|---|---|
| Primers (5'-3') | | | |
| Sense | GGAGTTCAAG AAGGAGTTTC | AGGGATTTGA ATCATGTTTG | CTGGACCAA ACACAAATG |
| Antisense | CCACATACAG TGTCTGGTA | CTGCTAGTTC TTTACTGGC | ATGCCTTCTT TCACCTTC |
| Probe | CCGCTTACGCC AGAGGAACT | TGTAGATTCAACTT GCCGCTGTC | TTGCCATCCAGC CACTCAGT |
| Dye | 5'-FAM | 5'-HEX | 5'-Texas red |
| Quencher | 3'-BHQ1 | 3'-BHQ1 | 3'-BHQ2 |
| Product size (bp) | 149 | 121 | 100 |

REFERENCES

Andersen H L, Kilpatrick I C. Prevention by (+/−)-8-hydroxy-2-(di-n-propylamino)tetralin of both catalepsy and the rises in rat striatal dopamine metabolism caused by haloperidol. Br J Pharmacol 1996; 118(2):421-7.

Brod et al. (2000) Annals of Neurology, 47:127-131.

Burgunder J M, Guttman M, Perlman S, Goodman N, van Kammen D P, Goodman L. An International Survey-based Algorithm for the Pharmacologic Treatment of Chorea in Huntington's Disease. PLoS Curr 2011; 3:RRN1260.

Chomczynski, P. & Sacchi, N. Anal. Biochem. 162: 156-159, 1987 Dyhring T, Nielsen E O, Sonesson C, Pettersson F, Karlsson J, Svensson P, et al. The dopaminergic stabilizers Pridopidine (ACR16) and (−)-OSU6162 display dopamine D(2) receptor antagonism and fast receptor dissociation properties. Eur J Pharmacol 2010; 628(1-3): 19-26.

Gronier B, Waters N, Ponten H, Klamer D, Waters S, Tedroff J. Pridopidine increases glutamatergic neuron firing in the frontal cortex. In: International Congress of Parkinson's Disease and Movement Disorders 2012; 2012; Dublin, Ireland; 2012.

Guidance for Industry. In vivo drug metabolism/drug interaction studies—study design, data analysis, and recommendations for dosing and labeling, U.S. Dept. Health and Human Svcs., FDA, Ctr. for Drug Eval. and Res., Ctr. For Biologics Eval. and Res., Clin./Pharm., November 1999 <http://www.fda.gov/cber/gdlns/metabol.pdf>.

Jordan S, Koprivica V, Dunn R, Tottori K, Kikuchi T, Altar C A. In vivo effects of aripiprazole on cortical and striatal dopaminergic and serotonergic function. Eur J Pharmacol 2004; 483(1):45-53.

Kawashima T, Okuno H, Nonaka M, Adachi-Morishima A, Kyo N, Okamura M, et al. Synaptic activity-responsive element in the Arc/Arg3.1 promoter essential for synapse-to-nucleus signaling in activated neurons. Proc Natl Acad Sci USA 2009; 106(1):316-21.

Kleinschmidt-DeMasters et al. (2005) New England Journal of Medicine, 353:369-379.

Langer-Gould et al. (2005) New England Journal of Medicine, 353:369-379.

Natesan S, Svensson K A, Reckless G E, Nobrega J N, Barlow K B, Johansson A M, et al. The dopamine stabilizers (S)-(−)-(3-methanesulfonyl-phenyl)-1-propyl-piperidine [(−)-OSU6162] and 4-(3-methanesulfonylphenyl)-1-propyl-piperidine (ACR16) show high in vivo D2 receptor occupancy, antipsychotic-like efficacy, and low potential for motor side effects in the rat. J Pharmacol Exp Ther 2006; 318(2):810-8.

Nilsson M, Carlsson A, Markinhuhta K R, Sonesson C, Pettersson F, Gullme M, et al. The dopaminergic stabiliser ACR16 counteracts the behavioural primitivization induced by the NMDA receptor antagonist MK-801 in mice: implications for cognition. Prog Neuropsychopharmacol Biol Psychiatry 2004; 28(4):677-85.

Paleacu D. Tetrabenazine in the treatment of Huntington's disease. Neuropsychiatr Dis Treat 2007; 3(5):545-51.

Pettersson F, Ponten H, Waters N, Waters S, Sonesson C. Synthesis and evaluation of a set of 4-phenylpiperidines and 4-phenylpiperazines as D2 receptor ligands and the discovery of the dopaminergic stabilizer 4-[3-(methylsulfonyl)phenyl]-1-propylpiperidine (huntexil, Pridopidine, ACR16). J Med Chem 2010; 53(6):2510-20.

Ponten H, Sonniksen K, Abrahamsson T, Waters N, Gustafsson B, Hanse E, et al. Behavioral and neurochemical repercussions of hippocampal network activity blockade during the neonatal period. Brain Res Dev Brain Res 2005; 155(1):81-6.

Ponten H, Kullingsjo J, Lagerkvist S, Martin P, Pettersson F, Sonesson C, et al. In vivo pharmacology of the dopaminergic stabilizer Pridopidine. Eur J Pharmacol 2010; 644 (1-3):88-95.

Reches A, Burke R E, Kuhn C M, Hassan M N, Jackson V R, Fahn S. Tetrabenazine, an amine-depleting drug, also blocks dopamine receptors in rat brain. J Pharmacol Exp Ther 1983; 225(3):515-21.

Roffler-Tarlov S, Sharman D F, Tegerdine P. 3,4-dihydroxyphenylacetic acid and 4-hydroxy-3-methoxyphenylacetic acid in the mouse striatum: a reflection of intra- and extra-neuronal metabolism of dopamine? Br J Pharmacol 1971; 42(3):343-51.

Satou T, Anderson A J, Itoh T, Tamai Y, Hayashi Y, Hashimoto S. Repetitive administration of Tetrabenazine induces irreversible changes in locomotion and morphology of the substantia nigra in ras. Exp Toxicol Pathol 2001; 53(4):303-8.

Schaefer G J, Michael R P. Drug interactions on spontaneous locomotor activity in rats. Neuroleptics and amphetamine-induced hyperactivity. Neuropharmacology 1984; 23(8):909-14.

Steward O, Worley P F. Selective targeting of newly synthesized Arc mRNA to active synapses requires NMDA receptor activation. Neuron 2001; 30(1):227-40.

Vollmer et al. (2008) "Glatiramer acetate after induction therapy with mitoxantrone in relapsing multiple sclerosis" Multiple Sclerosis, 00:1-8.

FDA Label for XENAZINE (Tetrabenzine) Jul. 6, 2011

The invention claimed is:

1. A method of treating a subject afflicted with a movement disorder comprising administering to the subject an amount of Tetrabenazine or a pharmaceutically acceptable salt thereof, and an amount of Pridopidine or a pharmaceutically acceptable salt thereof; wherein the method reduces depression induced by Tetrabenazine and/or improves functional capacity decline induced by Tetrabenazine and/or improves motor deficits induced by Tetrabenazine.

2. The method of claim 1, wherein the amounts when taken together are more effective to treat the subject than when each agent at the same amount is administered alone.

3. A method of reducing or preventing one or more side effects of periodic administration of an amount of Tetrabenazine or a pharmaceutically acceptable salt thereof to a subject, comprising periodically administering to the subject an amount of Pridopidine or a pharmaceutically acceptable salt thereof.

4. The method of claim 3, wherein the one or more side effects are selected from depression, suicidality, akathisia, restlessness, agitation, parkinsonism, sedation, somnolence, and dysphagia.

5. The method of claim 3, wherein the subject is afflicted with a movement disorder.

6. The method of claim 1, wherein the amount of Tetrabenazine or a pharmaceutically acceptable salt thereof is administered via oral administration.

7. The method of claim 1, wherein the amount of Tetrabenazine or a pharmaceutically acceptable salt thereof is administered daily, twice daily or three times daily.

8. The method of claim 1, wherein the amount of Tetrabenazine or a pharmaceutically acceptable salt thereof is 0.05 mg/kg per day to 0.20 mg/kg per day.

9. The method of claim 1, wherein the amount of Tetrabenazine or a pharmaceutically acceptable salt thereof is 1-500 mg/day.

10. The method of claim 1, wherein the amount of Pridopidine or a pharmaceutically acceptable salt thereof is administered via oral administration.

11. The method of claim 1, wherein the amount of Pridopidine or a pharmaceutically acceptable salt thereof is administered daily or twice daily.

12. The method of claim 1, wherein the amount of Pridopidine or a pharmaceutically acceptable salt thereof is 1.5 µmol/kg per day to 20 µmol/kg per day.

13. The method of claim 1, wherein the amount of Pridopidine or a pharmaceutically acceptable salt thereof is 1-500 mg/day.

14. The method of claim 1, wherein the movement disorder is Huntington's disease, Tourette's syndrome, or tardive dyskinesia.

15. The method of claim 1, wherein the amount of Tetrabenazine or a pharmaceutically acceptable salt thereof and the amount of Pridopidine or a pharmaceutically acceptable salt thereof is effective to alleviate a symptom of the movement disorder.

16. The method of claim 15, wherein the symptom is chorea.

17. The method of claim 1, wherein the subject is receiving Tetrabenazine therapy prior to initiating administration of Pridopidine or a pharmaceutically acceptable salt thereof.

18. The method of claim 1, wherein the amount of Tetrabenazine or a pharmaceutically acceptable salt thereof and the amount of Pridopidine or a pharmaceutically acceptable salt thereof are administered simultaneously.

19. The method of claim 1, wherein the subject is a human patient.

20. A pharmaceutical composition comprising an amount of Tetrabenazine or pharmaceutically acceptable salt thereof, an amount of Pridopidine or pharmaceutical acceptable salt thereof, and at least one pharmaceutical acceptable carrier.

21. The pharmaceutical composition of claim 20, wherein the amount of Tetrabenazine or pharmaceutically acceptable salt thereof is 5-100 mg.

22. The pharmaceutical composition of claim 20, wherein the amount of Pridopidine or pharmaceutical acceptable salt thereof is 10-100 mg.

23. The method of claim 3, wherein the amount of Tetrabenazine or a pharmaceutically acceptable salt thereof is administered via oral administration.

24. The method of claim 3, wherein the amount of Tetrabenazine or a pharmaceutically acceptable salt thereof is administered daily, twice daily or three times daily.

25. The method of claim 3, wherein the amount of Tetrabenazine or a pharmaceutically acceptable salt thereof is 0.05 mg/kg per day to 0.20 mg/kg per day.

26. The method of claim 3, wherein the amount of Tetrabenazine or a pharmaceutically acceptable salt thereof is 1-500 mg/day.

27. The method of claim 3, wherein the amount of Pridopidine or a pharmaceutically acceptable salt thereof is administered via oral administration.

28. The method of claim 3, wherein the amount of Pridopidine or a pharmaceutically acceptable salt thereof is administered daily or twice daily.

29. The method of claim 3, wherein the amount of Pridopidine or a pharmaceutically acceptable salt thereof is 1.5 µmol/kg per day to 20 µmol/kg per day.

30. The method of claim 3, wherein the amount of Pridopidine or a pharmaceutically acceptable salt thereof is 1-500 mg/day.

31. The method of any one of claim 5, wherein the movement disorder is Huntington's disease, Tourette's syndrome, or tardive dyskinesia.

32. The method of claim 3, wherein the amount of Tetrabenazine or a pharmaceutically acceptable salt thereof and the amount of Pridopidine or a pharmaceutically acceptable salt thereof is effective to alleviate a symptom of the movement disorder.

33. The method of claim 32, wherein the symptom is chorea.

34. The method of claim 3, wherein the subject is receiving Tetrabenazine therapy prior to initiating administration of Pridopidine or a pharmaceutically acceptable salt thereof.

35. The method of claim 3, wherein the amount of Tetrabenazine or a pharmaceutically acceptable salt thereof and the amount of Pridopidine or a pharmaceutically acceptable salt thereof are administered simultaneously.

36. The method of claim 3, wherein the subject is a human patient.

* * * * *

SEQUENCE LISTING

```
<160> NUMBER OF SEQ ID NOS: 15

<210> SEQ ID NO 1
<211> LENGTH: 20
<212> TYPE: DNA
<213> ORGANISM: Artificial Sequence
<220> FEATURE:
<223> OTHER INFORMATION: Sense, Activity-regulated gene, Accession
      Number U19866

<400> SEQUENCE: 1
ggagttcaag aaggagtttc                                              20

<210> SEQ ID NO 2
<211> LENGTH: 19
<212> TYPE: DNA
<213> ORGANISM: Artificial Sequence
<220> FEATURE:
<223> OTHER INFORMATION: Antisense, Activity-regulated gene, Accession
      Number U19866

<400> SEQUENCE: 2
ccacatacag tgtctggta                                               19
```

-continued

<210> SEQ ID NO 3
<211> LENGTH: 20
<212> TYPE: DNA
<213> ORGANISM: Artificial Sequence
<220> FEATURE:
<223> OTHER INFORMATION: Probe, Activity-regulated gene, Accession
      Number U19866

<400> SEQUENCE: 3
ccgcttacgc cagaggaact                                                 20

<210> SEQ ID NO 4
<211> LENGTH: 20
<212> TYPE: DNA
<213> ORGANISM: Artificial Sequence
<220> FEATURE:
<223> OTHER INFORMATION: Sense, Hypoxantine phosphoribosyl transferase,
      Accession Number AF001282

<400> SEQUENCE: 4
agggatttga atcatgtttg                                                 20

<210> SEQ ID NO 5
<211> LENGTH: 19
<212> TYPE: DNA
<213> ORGANISM: Artificial Sequence
<220> FEATURE:
<223> OTHER INFORMATION: Antisense, Hypoxantine phosphoribosyl
      transferase, Accession Number AF001282

<400> SEQUENCE: 5
ctgctagttc tttactggc                                                  19

<210> SEQ ID NO 6
<211> LENGTH: 23
<212> TYPE: DNA
<213> ORGANISM: Artificial Sequence
<220> FEATURE:
<223> OTHER INFORMATION: Probe, Hypoxantine phosphoribosyl transferase,
      Accession Number AF001282

<400> SEQUENCE: 6
tgtagattca acttgccgct gtc                                             23

<210> SEQ ID NO 7
<211> LENGTH: 18
<212> TYPE: DNA
<213> ORGANISM: Artificial Sequence
<220> FEATURE:
<223> OTHER INFORMATION: Sense, Cyclophilin A, Accession Number M19533

<400> SEQUENCE: 7
ctggaccaaa cacaaatg                                                   18

<210> SEQ ID NO 8
<211> LENGTH: 18
<212> TYPE: DNA
<213> ORGANISM: Artificial Sequence
<220> FEATURE:
<223> OTHER INFORMATION: Antisense, Cyclophilin A, Accession Number
      M19533

<400> SEQUENCE: 8
atgccttctt tcaccttc                                                   18

```
<210> SEQ ID NO 9
<211> LENGTH: 20
<212> TYPE: DNA
<213> ORGANISM: Artificial Sequence
<220> FEATURE:
<223> OTHER INFORMATION: Probe, Cyclophilin A, Accession Number M19533

<400> SEQUENCE: 9
ttgccatcca gccactcagt                                               20

<210> SEQ ID NO 10
<211> LENGTH: 20
<212> TYPE: DNA
<213> ORGANISM: Artificial Sequence
<220> FEATURE:
<223> OTHER INFORMATION: Sense, Hypoxantine phosphoribosyl transferase,
      Accession Number AF001282

<400> SEQUENCE: 10
ggccagactt gttggatttg                                               20

<210> SEQ ID NO 11
<211> LENGTH: 20
<212> TYPE: DNA
<213> ORGANISM: Artificial Sequence
<220> FEATURE:
<223> OTHER INFORMATION: Antisense, Hypoxantine phosphoribosyl
      transferase, Accession Number AF001282

<400> SEQUENCE: 11
ccgctgtctt ttaggctttg                                               20

<210> SEQ ID NO 12
<211> LENGTH: 20
<212> TYPE: DNA
<213> ORGANISM: Artificial Sequence
<220> FEATURE:
<223> OTHER INFORMATION: Sense, Cyclophilin A, Accession Number M19533

<400> SEQUENCE: 12
gtctcttttc gccgcttgct                                               20

<210> SEQ ID NO 13
<211> LENGTH: 20
<212> TYPE: DNA
<213> ORGANISM: Artificial Sequence
<220> FEATURE:
<223> OTHER INFORMATION: Antisense, Cyclophilin A, Accession Number
      M19533

<400> SEQUENCE: 13
gtctcttttc gccgcttgct                                               20

<210> SEQ ID NO 14
<211> LENGTH: 25
<212> TYPE: DNA
<213> ORGANISM: Artificial Sequence
<220> FEATURE:
<223> OTHER INFORMATION: Sense, Activity-regulated gene, Accession
      Number U19866

<400> SEQUENCE: 14
tctgctgtct ttggaacttt gtctg                                         25
```

```
<210> SEQ ID NO 15
<211> LENGTH: 25
<212> TYPE: DNA
<213> ORGANISM: Artificial Sequence
<220> FEATURE:
<223> OTHER INFORMATION: Antisense, Activity-regulated gene, Accession
      Number U19866

<400> SEQUENCE: 15
tctgctgtct ttggaacttt gtctg                                    25
```